United States Patent
Lucas

[11] Patent Number: 6,140,057
[45] Date of Patent: Oct. 31, 2000

[54] METHOD FOR DETECTING A PERICENTRIC INVERSION IN A CHROMOSOME

[75] Inventor: Joe N. Lucas, San Ramon, Calif.

[73] Assignee: The Regents of the University of California, Oakland, Calif.

[21] Appl. No.: 09/304,396

[22] Filed: May 4, 1999

Related U.S. Application Data

[60] Division of application No. 08/997,231, Dec. 23, 1997, Pat. No. 6,043,037, which is a continuation-in-part of application No. 08/703,302, Aug. 26, 1996, Pat. No. 5,731,153, which is a continuation-in-part of application No. 08/384,497, Feb. 6, 1995, Pat. No. 5,783,387.

[51] Int. Cl.⁷ ............................. C12Q 1/68; C07H 21/04
[52] U.S. Cl. .............................. 435/6; 436/94; 536/24.3; 536/24.31
[58] Field of Search ................... 435/6, 810; 436/94; 536/24.3, 24.31

[56] References Cited

U.S. PATENT DOCUMENTS

| | | | |
|---|---|---|---|
| 5,759,781 | 6/1998 | Ward et al. | 435/6 |
| 5,792,610 | 8/1998 | Witney et al. | 435/6 |
| 5,817,462 | 10/1998 | Garini et al. | 435/6 |
| 5,936,731 | 8/1999 | Cabib et al. | 356/346 |

OTHER PUBLICATIONS

Lucas et al., Inc. J. Radiat. Biol. 71(1), 29–33 (Jan. 1997).

Primary Examiner—Kenneth R. Horlick
Attorney, Agent, or Firm—L. E. Carnahan; Alan H. Thompson; Daryl S. Grzybicki

[57] ABSTRACT

A method is provided for determining a clastogenic signature of a sample of chromosomes by quantifying a frequency of a first type of chromosome aberration present in the sample; quantifying a frequency of a second, different type of chromosome aberration present in the sample; and comparing the frequency of the first type of chromosome aberration to the frequency of the second type of chromosome aberration. A method is also provided for using that clastogenic signature to identify a clastogenic agent or dosage to which the cells were exposed.

17 Claims, 8 Drawing Sheets

METHOD FOR DETECTING A PERICENTRIC INVERSION IN A CHROMOSOME

RELATIONSHIP TO COPENDING APPLICATIONS

This application is a division of U.S. patent application Ser. No. 08/997,231, filed Dec. 23, 1997, now U.S. Pat. No. 6,043,037, which is a continuation-in-part of U.S. patent application Ser. No. 08/703,302, filed Aug. 26, 1996, now U.S. Pat. No. 5,731,153 issued Mar. 24, 1998 which is a continuation-in-part of U.S. patent application Ser. No. 08/384,497, filed Feb. 6, 1995, now U.S. Pat. No. 5,783,387 issued Jul. 21, 1998, each of which are incorporated herein by reference.

The United States government has rights in this invention pursuant to Contract Number W-7405-ENG48 between the United States Department of Energy and the University of California for the operation of Lawrence Livermore National Laboratory.

BACKGROUND OF THE INVENTION

1. Field of the Invention

The present invention relates to methods for identifying pericentric inversions and incomplete chromosome exchanges as well as methods for identifying clastogenic agents based on relationships between frequencies of different chromosome aberrations.

2. Description of Related Art

Chromosome aberrations refer to rearrangements between chromosomes (interchromosomal) and/or rearrangements within a chromosome (intrachromosomal). FIGS. 1B–1F illustrate several different chromosome aberrations which a pair of chromosomes, illustrated in FIG. 1A, can undergo. The pair of chromosomes illustrated in FIG. 1A include a first chromosome 12 and a second chromosome 12'. Each chromosome includes a centromere 14, 14', and chromatids 15 including telomeric regions (16A, 16B, 16A' and 16B'). FIG. 1B illustrates a simple translocation between chromosomes 12 and 12' where a chromatid on the first chromosome is exchanged with a chromatid on the second chromosome. FIGS. 1C and 1D illustrate types of incomplete translocations. As illustrated in FIG. 1C, a portion of a chromatid from the second chromosome 12' has been transferred to the first chromosome 12 while a portion of the first chromosome has been lost. As illustrated in FIG. 1D, a portion of a chromatid from the second chromosome 12' has been transferred to the first chromosome 12 while most of the second chromosome has been lost including centromere 14. FIG. 1E is a representation of a dicentric chromosome and a chromosome fragment produced by an aberration. FIG. 1F is a representation of a reciprocal dicentric translocation.

A chromosome translocation is one particular type of chromosome aberration. A chromosome translocation refers to the movement of a portion of one chromosome to another chromosome (interchromosome rearrangement) as well as the movement of a portion of a chromosome to a different location on that chromosome (intrachromosome rearrangement;. In general, chromosome translocations are characterized by the presence of a DNA sequence on a particular chromosome that is known to be native to a different chromosome or a different portion of the same chromosome.

Two chromosome translocations of particular note are dicentric and centric rings which are formed by the rejoining of the chromatids of two different chromosomes (interchromosome) and of the same chromosome (intrachromosome) respectively. Dicentric and centric rings are highly unstable and are almost always clonogenically fatal.

Symmetric translocations and pericentric inversions are more stable analogs of dicentric and centric rings. Analysis of banded chromosomes has been used to detect symmetric translocations and pericentric inversions. Banding analysis, however, is time consuming, making it ill suited for gathering statistically significant quantities of data, especially for inversions. Lucas, et al., *Rapid translocation frequency analysis in humans decades after exposure to ionizing radiation*, Int'l. J. Radiat. Biol., 62:53–63 (1992); Sachs, et al., Radiation Research, 133:345–350 (1993).

Incomplete reciprocal translocations, hereinafter referred to as "incompletes," are also stable translocations. Incompletes can be detected using chromosome painting where they appear as one bicolor and one solid color chromosome dterivative instead of two bicolor chromosome derivatives. It has been argued that incomplete reciprocal translocations are actually "hidden reciprocal translocations" due to one translocated segment being too small to detect. Kodama, et al. *Estimation of minimal size of translocated chromosome segment detectable by fluorescence in situ nybridization*, Int'l J. Radiat. Biol. 71:35 (1997). This problem cannot be resolved using conventional chromosome painting or banding because of the size resolution of the small translocated piece.

Clastogenic agents are chemicals, particles, or forms of energy which cause or enhance the frequency of chromosome aberrations. Examples of different types of clastogenic agents include, but are not limited to radioactive elements such as radon, uranium and hydrogen, their decay products and high energy particles they emit. Specific examples of radioactivity related clastogenic agents include gamma rays emitted from $^{60}$Co or $^{137}$Cs, $^{56}$Fe and $^{12}$C ions, and neutrons. Clastogenic agents can also be non-energy emitting chemicals such as benzene which can cause or enhance the frequency of chromosome aberrations.

Chromosome aberrations and the clastogenic agents which cause them or enhance their frequency are of interest due to the various cancers and other genetic diseases which are associated with chromosome aberrations. For exariple, radon and its decay products have been determined to be the major naturally occurring radioactive carcinogens in the human environment. Brenner, D. J., *Radon Risk and Remedy* 102. (W. H. Freeman. New York, 1989). It is believed that individuals receive high linear-energy-transfer (LET) charged-particle exposure from radon gases and its daughters. However, current risk estimates based on exposure to the(se particles are quite uncertain. A need exists for a method for determining which individuals, particularly those who later develop cancer, did, in fact, receive significant high-LET charged-particle radiation doses. A further need exists for a method for quantifying the amount of high-LET charged-particle radiation received. Nuclear dockyard workers who develop cancer after exposure to radiation would also benefit from a method which could be used to demonstrate a causal connection between their cancer and a high-LET radiation exposure. Lucas, J. N., et al. *Discrimination between leukemia- and non-leukemia-induced chromosomal abnormalities in the patient's lymphocytes*. Int'l. J. Radiat. Biol., 66:185–189 (1994).

Recent measurements of A-bomb dosimetry suggest that the neutron component may dominate the equivalent dose at relevant locations. Hoshi, M., et al. *Europium-152 activity* induced by Hiroshima atomic bomb neutrons. Comparison with the $^{32}P$, $^{60}Co$ and $^{152}Eu$ activities in Dosimetry System 1986 (DS86), Health Physics, 57:831–837 (1989). In the past year, there have been arguments advanced that most of the equivalent dose to which A-bomb survivors were exposed came from densely ionizing radiation (neutrons). A need has existed since 1945 for a method for identifying and quantifying neutron exposure for A-bomb survivors.

The need for methods for detecting aberrations and for associating the occurrence of particular aberrations with particular clastogenic agents and their dosages is evidenced by discussions in the following references: Savage, J. R. K. & Holloway, M., *Induction of sister-chromatic exchanges by d(42MeV)-Be neutrons in unstimulated human lymphocytes*, Brit. J. Radiol. 61:231–234 (1988); Kadhim, K. A., et al., *Transmission of chromosomal instability after plutonium alpha-particle irradiation*, Nature 355:738–740 (1992); Brenner, D. J. and Sachs, R. K., *Chromosomal "fingerprints" of prior exposure to densely ionizing radiation*, Radiation Research, 141):134–142 (1994).

SUMMARY OF THE INVENTION

A method is provided for detecting a pericentric inversion in a chromosome having a telomeric region, a subcentromeric region and a centromeric region by contacting a first probe having a sequence capable of selectively hybridizing to the telomeric region, a second probe having a sequence capable of selectively hybridizing to the subcentromeric region, and a third probe capable of selectively hybridizing to the centromeric region with the chromosome such that the first, second and third probes hybridize to the chromosome; determining a relative positioning of the first, second and third probes when hybridized to the chromosome; and detecting a pericentric inversion based on the relative positioning of the first, second and third probes.

In one embodiment, the telomeric region occurs on a first side of the centromeric region in a native state of the chromosome and a second side of the centromeric region when the chromosome has undergone a pericentric inversion, the step of determining the relative positioning including determining whether the telomeric region is on the second side of the centromeric region.

In another embodiment, the telomeric and subcentromic regions occur on a same side of the centromeric region in a native state of the chromosome and opposite sides of the centromeric region when the chromosome has undergone a pericentric inversion, the step of determining the relative positioning including determining whether the telomeric and subcentromic regions are on opposite sides of the centromeric region.

In yet another embodiment, the telomeric and subcentromic regions occur on opposite sides of the centromeric region in a native state of the chromosome and on a same side of the centromeric region chromosome has undergone a pericentric inversion, the step of determining the relative positioning including determining whether the telomeric and subcentromic regions are on the same side of the centromeric region.

The present invention also relates to a kit for detecting pericentric inversions in a chromosome. According to one embodiment, the kit includes a first probe having a sequence capable of selectively hybridizing to a telomeric region on either a first or second side of the chromosome relative to a centromeric region; a second probe having a sequence capable of selectively hybridizing to a subcentromeric region on either a first or second side of the chromosome relative to a centromeric region; and a third probe capable of selectively hybridizing to the centromeric region. In one variation of this embodiment, the first and second probes are capable of selectively hybridizing on a same side of the chromosome relative to the centromeric region. In another variation of this embodiment, the first and second probes are capable of selectively hybridizing on opposite sides of the chromosome relative to the centromeric region. The kit may optionally further include blocking DNA. The first, second and third probes may optionally each independently include a detectable marker.

A method is also provided for determining a clastogenic signature of a sample of chromosomes. According to one embodiment, the method includes quantifying a frequency of a first type of chromosome aberration present in the sample; quantifying a frequency of a second, different type of chromosome aberration present in the sample; and comparing the frequency of the first type of chromosome aberration to the frequency of the second type of chromosome aberration. The step of comparing may optionally include calculating a mathematical relationship between the frequency of the first and second types of chromosome aberrations.

A method is also provided for determining a clastogenic signature of a sample of chromosomes by quantifying a frequency of incomplete chromosome aberrations present in the sample; quantifying a frequency of complete chromosome aberrations present in the sample; and comparing the frequency of incomplete chromosome aberrations to the frequency of complete chromosome aberrations. The step of comparing may optionally include calculating a mathematical relationship between the frequency of complete chromosome aberrations and the frequency of incomplete chromosome aberrations. The step of quantifying incomplete aberrations may optionally include quantifying a frequency of terminal translocations, dicentric fragments, or combinations thereof present in the sample. The step of quantifying a frequency of terminal translocations may optionally include quantifying a centromere painted terminal aberrant chromosomes, non-centromere painted terminal aberrant chromosomes, or combinations thereof present in the sample. The step of quantifying a frequency of complete chromosome aberrations may optionally include quantifying a frequency of reciprocal translocations, reciprocal dicentric aberrant chromosomes, or combinations thereof present in the sample.

A method is also provided for identifying an exposure of a sample of chromosomes to a clastogenic a-gent. According to one embodiment of the method, the method includes quantifying a frequency of a first type of chromosome aberration present in the sample; quantifying a frequency of a second, different type of chromosome aberration present in the sample; forming a clastogenic signature for the sample based on a comparison of a relation between the frequency of the first type of chromosome aberration to the frequency of the second type of chromosome aberration to a relationship; and comparing the clastogenic signature for the sample to clastogenic signatures of one or more clastogenic agents. The relationship may optionally be a mathematical relationship between the frequency of the first and second types of chromosome aberrations. The relationship may also optionally be a ratio between the frequency of the first and second types of chromosome aberrations.

A method is also provided for identifying an exposure of a sample of chromosomes to a clastogenic agent. According to one embodiment, the method includes quantifying a frequency of incomplete chromosome aberrations present in the sample; quantifying a frequency of complete chromosome aberrations present in the sample; forming a clastogenic signature for the sample based on a comparison of a relation between of incomplete chromosome aberrations to the frequency of complete chromosome aberrations; and comparing the clastogenic signature for the sample to clastogenic signatures of one or more clastogenic agents. The relationship may optionally be a mathematical relationship between the frequency of complete chromosome aberrations and the frequency of incomplete chromosome aberrations. The step of quantifying incomplete aberrations may optionally include quantifying a frequency of terminal translocations, dicentric fragments, or combinations thereof present in the sample. The step of quantifying a frequency of terminal translocations may optionally include quantifying a centromere painted terminal aberrant chromosomes, non-centromere painted terminal aberrant chromosomes, or combinations thereof present in the sample. The step of quantifying a frequency of complete chromosome aberrations may optionally include quantifying a frequency of reciprocal translocations, reciprocal dicentric aberrant chromosomes, or combinations thereof present in the sample.

The present invention also relates to a clastogenic signature for a clastogenic agent. In one embodiment, the signature is a relation between a frequency of incomplete chromosome aberrations to a frequency of complete chromosome aberrations in a sample of chromosomes which is characteristic of chromosomes in cells which has been exposed to the clastogenic agent.

A method is also provided for determining a dose of high LET radiation received by a sample of chromosomes. According to one embodiment of the method, the method includes quantifying a frequency of incomplete chromosome aberrations present in the sample; quantifying a frequency of complete chromosome aberrations present in the sample; and comparing a relationship between the frequency of incomplete chromosome aberrations to complete chromosome aberrations with relationships between the frequency of incomplete chromosome aberrations to complete chromosome aberrations for known dosages of high LET radiation.

A method is also provided for obtaining chromosome painting probes which selectively hybridize to a specific target chromosome. According to one embodiment of this method, the method includes contacting a target chromosome with a sample of painting probes under hybridizing conditions in the presence of blocking DNA, the painting probes including a mechanism for immobilizing chromosomes which hybridize to them; immobilizing those chromosomes which hybridize to a painting probe; and recovering the painting probe hybridized to the immobilized chromosomes. The present invention also relates to painting probes isolated according to this method.

A method is also provided for obtaining chromosome painting probes which selectively hybridize to a specific target chromosome. According to one embodiment, the method includes contacting a target chromosome with a sample of painting probes under hybridizing conditions in the presence of a unique sequence probe which includes a mechanism for immobilizing chromosomes which hybridize to the unique sequence probe; immobilizing those chromosomes which hybridize to the unique sequence probe, immobilization of the chromosomes also immobilizing painting probes which are hybridized to the chromosomes; isolating the immobilized painting probes and unique sequence probes from the immobilized chromosomes; and isolating the immobilized painting probes from the unique sequence probes. The present invention also relates to painting probes isolated according to this method.

BRIEF DESCRIPTION OF THE DRAWINGS

FIGS. 1A–1F illustrate a series of different chromosome aberrations wherein:

FIG. 1A illustrates a pair of chromosomes which have not undergone an aberration;

FIG. 1B illustrates an apparently simple translocation;

FIGS. 1C and 1D illustrate different types of incomplete translocations;

FIG. 1E is a representation of a dicentric and a fragment; and

FIG. 1F is a representation of a reciprocal dicentric translocation.

FIG. 2A illustrates a chromosome having first and second telomeric regions, first and second subcentromeric regions, and a centromere.

FIG. 2B illustrates the chromosome illustrated in FIG. 1A after having undergone a pericentric inversion.

FIG. 3A illustrates an embodiment of the method in which the inversion is detected using probes which detect the movement of a telomeric region that is on the same side of a centromere as a subcentromeric region in the native state of the chromosome to the opposite side of the centromere after the inversion.

FIG. 3B illustrates an embodiment of the method in which the inversion is detected using probes which detect the movement of a telomeric region that is on the opposite side of a centromere as a subcentromeric region in the native state of the chromosome to the same side of the centromere after the inversion.

FIG. 9A shows a chromosome after hybridization.

FIG. 9B shows a translocated chromosome derivative.

FIG. 9C shows another translocated chromosome derivative.

FIG. 9D is a representation of a non-hybridized chromosome.

FIG. 10A shows trapping of normal and translocated chromosome.

FIG. 10B illustrates release of chromosomes from the magnetic solid support.

FIGS. 10C and 10D illustrate different embodiments of the invention.

DETAILED DESCRIPTION OF THE INVENTION

Figures 1A, 1B, 1C:
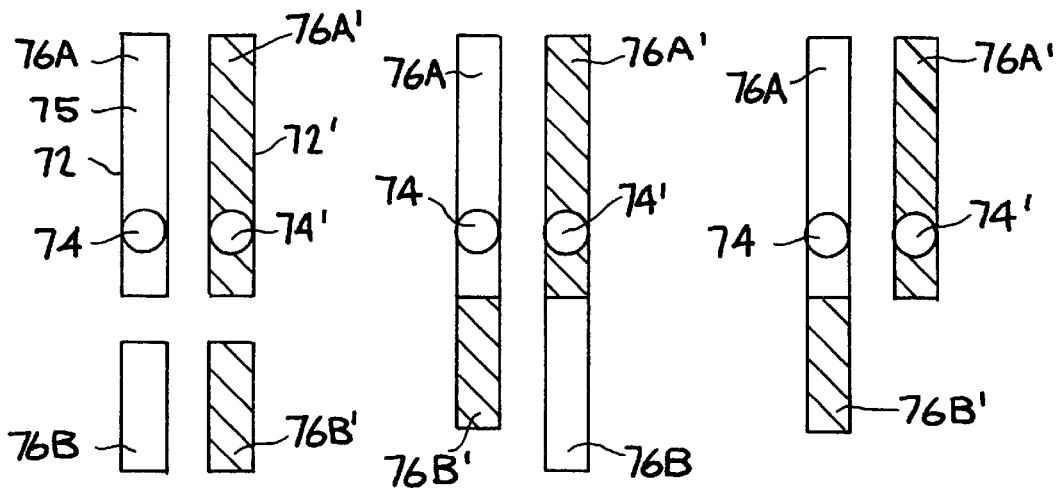

The present invention relates to methods and kits for determining a clastogenic signature for a sample of cells. As will be discussed below in more detail, a clastogenic signature is a relationship between a frequency of a first type of chromosome aberration and a frequency of a second different type of chromosome aberration which is characteristic of chromosomes from a sample of cells which have been exposed to a particular type of clastogenic agent or a particular dosage of a clastogenic agent.

In one embodiment, the clastogenic signature is a relationship between the number of incomplete chromosome aberrations to complete chromosome aberrations in a sample of cells and is useful for identifying whether the cells were exposed to high-LET radiation.

The present invention also relates to methods and kits for determining whether a sample of c(ells has been exposed to a clastogenic agent by determining a relationship between a frequency of a first type of chromosome aberration and a frequency of a second different type of chromosome aberration for a sample of cells and comparing the determined relationship to clastogenic signatures for different clastogenic agents.

The present invention also relates to methods and kits for detecting pericentric inversions in a sample of chromosomes using a series of probes which hybridize to different specific regions of the chromosome, i.e., telomeric region, subcentromeric region and centromeric region. As will be discussed below in more detail, pericentric inversions are detected by determining a relative positioning of the series of probes when hybridized to a chromosome.

The present invention also relates to methods and kits for obtaining specific painting probes which can be used for performing chromosome painting. As will be discussed below in more detail, specific painting probes provide several advantages over blocking DNA which has been used in chromosome painting assays.

1. Detection of Chromosome Aberrations Using Fish

A variety of methods have been developed for detecting chromosome aberrations. For example, fluorescence in situ hybridization (FISH), also commonly referred to as "chromosome painting", is an assay for detecting interchromosome translocations. FISH is described in Pinkel, et al., Proc. Natl. Acad. Sci. (USA) 83:2934–2938 (1986),; Lucas, et al., Int'l J. Radiat. Biol. 56:35–44 (1989), 62:53–63 (1992); and Pinkel, et al., Proc. Natl. Acad. Sci. (USA) 85:9138–9142 (1988).

The fluorescent hybridization "painting" probes used in FISH-based chromosome painting are preferably chromosome-specific, i.e., each probe hybridizes to or paints a particular chromosome. Interchromosome translocations are identified in the FISH assay by visually scanning individual cells for the presence of two different fluorescent signals on the same chromosome. According to the FISH assay, the two fluorescent signals originate from two different FISH probes, each probe indicating the presence of a sequence from a different chromosome.

Because FISH chromosome painting involves probes that hybridize to an entire chromosome or a large portion of a chromosome, the FISH assay is not designed to detect interchromosome translocations, such as a pericentric inversion. Also, because of the limited visual resolution of chromosome painting (See Kodama, et al., *Estimation of minimal size of translocated chromosome segment detectable by fluorescence in situ hybridization*, Int'l J. Radiat. Biol. 71:35 (1997), incompletes can be difficult to distinguish from complete exchanges having small translocated segments with certainty.

2. Method for Detecting Pericentric Inversions

Figure 2B:
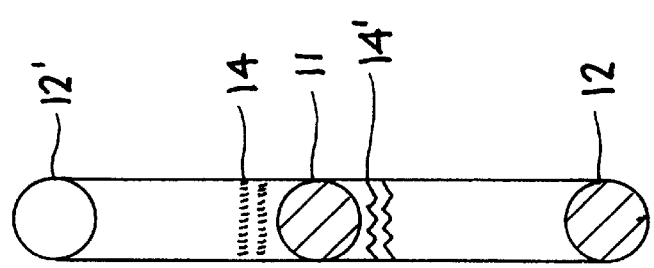
FIGS. 2A–B illustrate the change in chromosome structure as a result of a pericentric inversion.
Figure 2A:
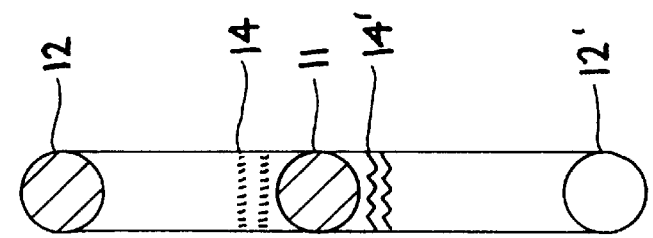

One aspect of the present invention relates to a method and kits for detecting pericentric inversions. FIGS. 2A–B illustrate the structure of a chromosome before and after undergoing a pericentric inversion. As illustrated in FIG. 2A, a chromosome includes a centromere 11, first and second telomeric regions 12, 12' on either side of the centromere, and first and second subcentromeric regions 14, 14' on either side of the centromere. FIG. 2B illustrates the structure of the chromosome illustrated in FIG. 2A after undergoing a pericentric inversion. As illustrated in FIG. 2B, when the chromosome undergoes a pericentric inversion, telomeric regions 12, 12' move to the opposite sides of the chromosome relative to where the telomeric regions 12, 12' were before the inversion. Thus, as illustrated in FIGS. 2A–2B, a pericentric inversion can be characterized by the movement of a telomeric region 12 (12') that is on the same side of a centromere 11 as a subcentromeric region 14 (14') in the native state of the chromosome to the opposite side of the centromere 11 after the inversion. Similarly, a pericentric inversion can also be characterized by the movement of a telomeric region 12 (12') that is on the opposite side of a centromere 11 as a subcentromeric region 14' (14) in the native state of the chromosome to the same side of the centromere 11 after the inversion.

The method of the present invention enables the detection of pericentric inversions in chromosomes using three probes: one which selectively hybridizes to a telomeric region (12 or 12'); one which selectively hybridizes to a subcentromeric region (14 or 14'); and one which selectively hybridizes to the centromere 11. By monitoring the relative positioning of the hybridization probes on the chromosome, the presence of a pericentric inversion can be detected.

According to the method, a chromosome is contacted under conditions favorable for hybridization with first, second and third probes such that the probes hybridize to complementary regions on the chromosome. Suitable conditions for conducting a hybridization are described in Pinkel, et al., Proc. Natl. Acad. Sci. (USA) 83:2934–2938 (1986); Lucas, et al., Int'l. J. Radiat. Biol. 56:3544 (1989), 62:53–63 (1992); and Pinkel, et al., Proc. Natl. Acad. Sci. (USA) 85:9138–9142 (1988).

The first probe includes a sequence capable of selectively hybridizing to one of the two telomeric regions that naturally occur on either side of the centromere of a chromosome. The second probe includes a sequence capable of selectively hybridizing to a subcentromeric region that naturally occurs either on the same side or the opposite side of the centromere as the telomeric region to which the first hybridization probe hybridizes. The third probe includes a sequence capable of selectively hybridizing to the centromere.

After hybridization, the chromosome is examined to determine the relative positioning of the first, second and third probes on the chromosome. A pericentric inversion is detected when the positioning of the telomeric region and subcentromeric region relative to the centromere does not correspond to the native state of the chromosome (e.g., the telomeric and subcentrorreric regions move from opposite sides of the centromere to the same side of the centromere or from the same side of the centromere to opposite sides of the centromere).

Determination of the relative positioning of the first, second and third probes on the chromosome is preferably done with the assistance of detectable markers attached to the probes. As described herein, attachment of the detectable markers to the probes may be performed either before or after hybridization.

It is preferred that the detectable markers be visually detectable (e.g. colored dyes or fluorescent dyes) so that the three probes, when hybridized to the chromosome, create a visually detectable pattern. The visually detectable pattern generated by the detectable markers provides the user with a clear indicator of whether a particular chromosome includes a pericentric inversion. As a result, the method provides little room for scoring error and requires a low level of technical scoring knowledge. In addition, the clarity of the inversion indicator enables more rapid scoring to be performed.

Figure 3A:
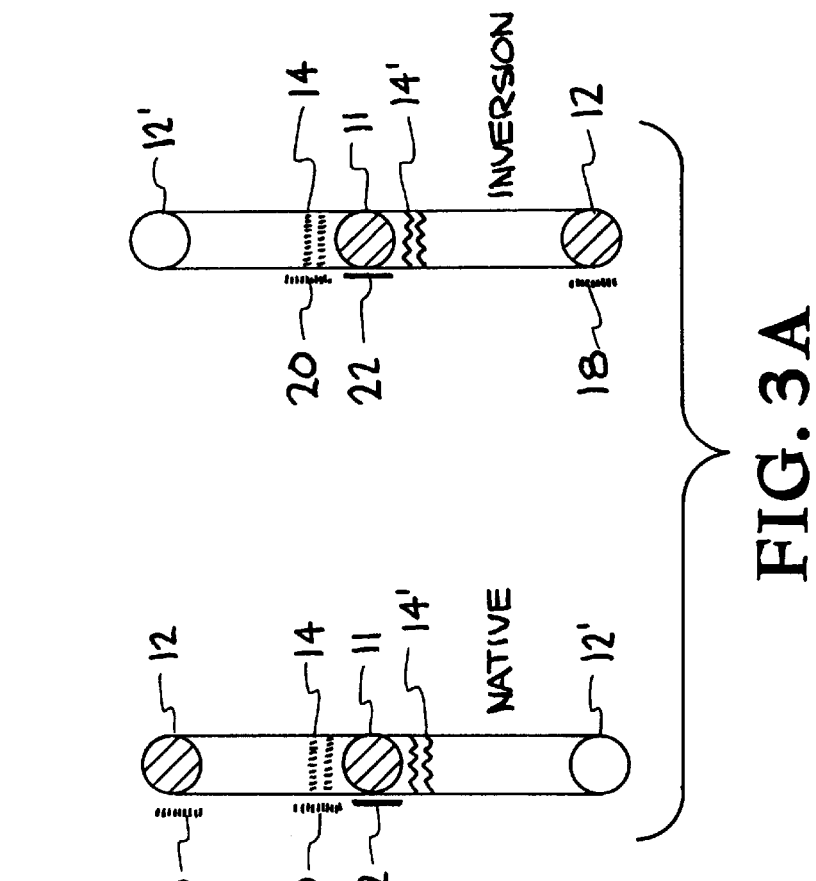
FIGS. 3A–B illustrate two embodiments of the method according to the present invention.
Figure 3B:
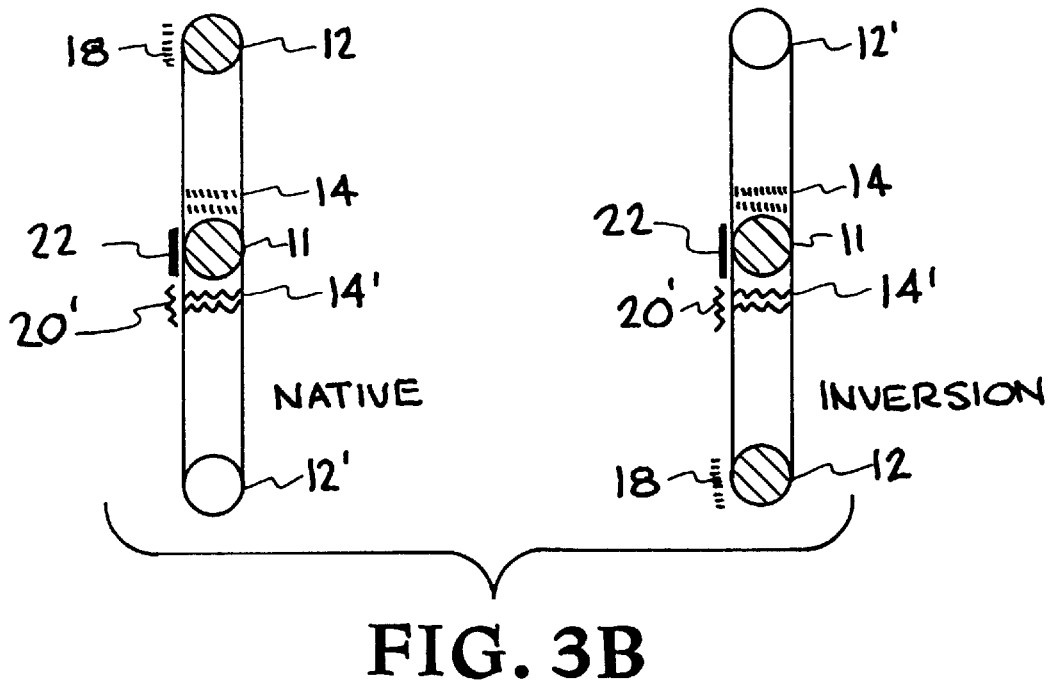

FIGS. 3A–B illustrate two embodiments of the method according to the present invention. FIG. 3A illustrates one embodiment of the method in which the inversion is detected based on the movement of a telomeric region 12 that is on the same side of a centromere 11 as a subcentromeric region 14 in the native state of the chromosome to the opposite side of the centromere 11 after the inversion. As illustrated in FIG. 3A, three hybridization probes are used. The first probe 18 has a first detectable marker and is hybridized to telomeric region 12. The second probe 20 has a second detectable marker and is hybridized to subcentromeric region 14. The third probe 22 has a third detectable marker and is hybridized to the centromere 24. As can be seen in FIG. 3A, a pericentric inversion is detected when the pattern of detectable markers on the probes indicates that the telomeric region 12 and subcentromeric region 14 are on opposite sides of the centromere. Meanwhile, a chromosome in its native state is detected when the pattern of the detectable markers show that the telomeric region 12 and subcentromeric region 14 are on same side of the centromere.

FIG. 3B illustrates another embodiment of the method in which the inversion is detected based on the movement of a telomeric region 12 that is on the opposite side of a centromere 11 as a subcentromeric region 14' in the native state of the chromosome to the same side of the centromere 11 after the inversion. As illustrated in FIG. 3B, three hybridization probes are used. The first probe 18 has a first detectable marker and is hybridized to telomeric region 12. The second probe 20' has a second detectable marker and is hybridized to subcentromeric region 14'. The third probe 22 has a third detectable marker and is hybridized to the centromere 24. As can be seen in FIG. 3B, a pericentric inversion is detected when the pattern formed by the detectable markers show that the telomeric region 12 and subcentromeric region 14' are on same side of the centromere. Meanwhile, a chromosome in its native state is detected when the pattern of the detectable markers show that the telomeric region 12 and subcentromeric region 14' are on opposite sides of the centromere.

As illustrated in FIG. 3A, two of the detectable markers used on the three probes may be the same. Alternatively, as illustrated in FIG. 3B, the detectable markers used on the three probes may all be different. With regard to the detectable markers used on the probes, it is desired that the combination of detectable markers produce a pattern which can be readily discernable to the person or machine scoring the chromosomes.

Another embodiment of the invention permits simultaneous detection of translocations and pericentric inversions. This is accomplished by using, in addition to the pericentric inversion probe, another probe that stains all telomeres in a color different from that used for the inversion probes.

Probes used in the method selectively hybridize to a particular telomeric region, subcentromeric region or centromeric region of a chromosome. A variety of sources exist for the nucleic acid sequences used in these probes to selectively hybridize to a particular telomeric region, subcentromeric region or centromeric region. For example, the probes may be prepared from PCR libraries. An exemplary method for preparing PCR libraries of individual chromosomes and the use of those libraries to prepare chromosome-specific hybridization probes is taught in Vooijs, et al. Am. J. Humr. Genet. 52:586–597 (1993).

Each probe preferably also includes a detectable marker. The detectable marker may be any marker which can be used to determine the relative position of the probe to other probes hybridized to the chromosome. The detectable marker is preferably a dye which can be seen under natural light or with the assistance of an excitation light source to cause fluorescence. In a preferred embodiment, the detectable marker is a fluorescent dye. Examples of fluorescent dyes that may be used include, but are not limited to fluorescein and its derivatives, rhodamine and its derivatives, dansyl, umbeliferone, acridimium, and chemiluminescent molecules such as luciferin and 2,3-dihydrophthalazinediones.

The detectable marker may Le attached to the probes either before or after hybridization to the chromosome. For example, the probe may include a molecule which binds to a detectable marker. According to this embodiment, the detectable marker may be covalently attached to or incorporated into probe after hybridization, for example, as taught by Ward, European Patent Application No. 63,879. In such instances, the probe is detected by adding the detectable marker which specifically binds to the probe, thereby enabling detection of the probe. Examples of such molecules and their analytically detectable counterparts include biotin and either fluorescent or chemiluminescent avidin. Antibodies that bind to an analytically detectable antigen may also be used as the detectable marker. The detectable marker may also be a molecule which, when subjected to chemical or enzymatic modification, becomes detectable such as those disclosed in Leary, et al., Proc. Natl. Acad. Sci. (U.S.A.), 80:4045–4049 (1983)

Suitable probes are described in Lucas, et al, *Rapid determination of human chromosome translocation frequency using a pair of chromosome-specific DNA probes*, Int'l J. Radiat. Biol. 56:35–44 (1989). In a preferred embodiment, the probe comprises as a marker 7-amino-4-methylcoumarin-3-acetic acid (AMCA), which is blue excited in the UV. Lucas, et al. *Rapid translocation frequency analysis in humans decades after exposure to ionizing radiation*, Int'l J. Radiat. Biol. 62:53–63 (1992). Suitable telomere probes are those that are commercially available (from ONCOR, for example) or those that can be generated using PCR, using, for example, the method of Ijdo et al. Nucleic Acids Research, 19, (1991). The telomere) probe sequences are $((TTAGGG)_5$ and $(CCCTM)_5)$.

3. Method for Detecting Incomplete Aberrations

The method of the present invention for detecting inversions can also be used to detect incomplete aberrations. An incomplete aberration is distinguished from a complete aberration by the absence of a telomere or terminal DNA translocated from another chromosome. The fluorescence pattern of a chromosome with an incomplete aberration lacks a fluorescent telomere signal, whereas a chromosome with a complete symmetric translocation has telomere signals on each telomeric end.

4. Method for Using Aberration Signature to Identify Clastogenic Agents

The present invention relates to clastogenic signatures which are characteristic of a particular type of clastogenic agent or a particular dosage of a clastogenic agent. In general, a clastogenic signature is a relationship between a frequency of a first type of chromosome aberration and a frequency of a second different type of chromosome aberration which is characteristic of chromosomes from a sample of cells which have been exposed to a particular type of clastogenic agent or a particular dosage of a clastogenic agent.

In one embodiment, the clastogenic signature is a relationship between the number of incomplete chromosome aberrations to complete chromosome aberrations in a sample of cells and is useful for identifying whether cells have been exposed to high-LET radiation.

The present invention also relates to a method for determining whether a sample of cells has been exposed to a clastogenic agent based on the clastogenic signature of the sample of cells. According to the method, a relationship between a frequency of a first type of chromosome aberration and a frequency of a second different type of chromosome aberration for a sample of cells is determined and then comparing to clastogenic signatures for different clastogenic agents and/or doses of clastogenic agents. In one embodiment, a method is provided for determining whether a sample of cells has been exposed to high-LET radiation based on a relationship between a frequency of complete chromosome aberrations and a frequency of incomplete chromosome aberrations.

Previously, it had been postulated that it is possible to identify whether a sample of cells were exposed to a particular type of clastogenic agent based on a frequency of different types of chromosome aberrations. For example, the ratio of interchromosomal to intrachromosomal exchanges (F value) has been proposed as a radiation signature. Brenner, D. J. and Sachs, R. K., *Chromosomal "fingerprints" of prior exposure to densely ionizing radiation*, Radiation Research, 140:134–142 (1994). However, results from more careful experiments designed to test this theory, together with an evaluation of past experimental data (Schmid and Bauchinger 1996) do not support a signature based on the ratio of interchromosomal to intrachromosome exchanges. Lucas, J. N., et al. *A rapid method for measuring pericentric inversions using fluorescence in situ hybridization (FISH)*, Int'l. J. Radiat. Biol., 71:29–33 (1997); Schmid, E. and Bauchinger, M., *Comments on "direct biological evidence for a significant neutron dose to survivors of the Hiroshima Atomic Bomb" by D. J. Brenner*, Radiation Research, 146:479–482 (1996).

Provided in the examples is data demonstrating that a stable, measurable biological signature for high LET radiation does exist. More specifically, as shown in Table 1, by comparing the frequency of complete chromosome aberrations to the frequency of incomplete chromosome aberrations in sample(s of cells exposed to high and low LET radiation, a useful clastogenic signature is revealed. In a preferred embodiment, this clastogenic signature is a ratio between the number of complete chromosomal aberrations and the number of incomplete chromosomal aberrations. In a more preferred embodiment, the clastogenic signature is a ratio between the number of reciprocal translocations and the number of terminal translocations. This ratio is referred to herein as the S ratio.

Of course, other statistically significant relationships besides the S ratio between a group of one or more types of chromosome aberrations and another group of one or more types of chromosome aberrations are believed to exist which can serve as meaningful signatures for identifying clastogenic agents and/or dosages of clastogenic agents and are intended to fall within the scope of the present invention. As technology for more precisely detecting different types of aberrations are developed and as relationships between the frequencies of different types of aberrations and different types or dosages of clastogenic agents are evaluated, further clastogenic signatures will be identified. For example, it is believed that harmonic functions or various polynomic functions may be useful for expressing a relationship between different types of aberrations.

There are several preferred ways for measuring complete and incomplete chromosome aberrations. For example, measurements that are usefully representative of the frequency of incomplete chromosomal aberrations include, but are not limited to the frequency of: centromere painted terminal aberrant chromosomes, non-centromere painted terminal aberrant chromosomes, and dicentric fragments. Measurements that are usefully representative of complete chromosomal aberrations include, but are not limited to the numbers of: reciprocal translocations, and reciprocal dicentric aberrant chromosomes. Of course, the specific measurements within the genus of incomplete and complete chromosomal aberrations can be combined in various ways in making the overall comparison that provides the clastogenic signature or permits a determination of a high LET dose.

It is noted that better methods for detecting different forms of complete and incomplete aberrations are expected to be developed. These methods may prove useful for enhancing the determination of a clastogenic signature by being able to more precisely identify different types of aberrations and by insuring that the different types of aberrations are accurately characterized.

S ratio measurements are simple to conduct because both incomplete aberrations and complete aberrations are easy to measure. Both types of aberrations occur at approximately the same frequency for high-LET radiation and are measured at the same time as each other using the same probe(s). Moreover, the large difference in the frequency of incomplete aberrations to complete aberrations makes it easy to distinguish between high- and low-LET contributions in many important exposure cases.

Examples of applications for clastogenic signatures include, but are not limited to: [1] A-bomb dosimetry: the neutron contribution to the dose for A-bomb survivors, [2] radon exposure: connecting late development of cancer with early exposure to high-LET radiation, [3] NASA space flights: exposures in free space and in the space station environment, and [4] national security: aid in identifying nuclear material smugglers irradiated by weapons-grade nuclear uranium (high-LET).

Detection of different types of aberrations can be performed by any method known in the art or developed in the future. Examples of some methods for detecting translocations are described in the section of this application regarding chromosome painting and FISH. Typically, translocations may be measured using modified fluorescence in-situ hybridization techniques.

It is believed that the incomplete-complete clastogenic signature identified is due to high-LET radiation producing a higher local density of double-strand breaks (DSBs) compared to low-LET radiation. As a result, competition leads to a greater chance of unrejoined chromosome ends for high-LET radiation. It is believed that this greater chance of unrejoined chromosome ends causes the frequency of compete aberrations relative incomplete aberrations to be statistically significantly higher for high-LET radiation, thus yielding a signature for high-LET radiation.

The relative local increase ir DSBs for high-LET radiation could allow for more unrejoined DSBs within the local exchange site. Complete reciprocal translocations have been found to be stable over time, Lucas, J. N., et al., *Stability of the translocation frequency following whole-body irradiation measured in rhesus monkeys*, Int'l. J. Radiat. Biol., 70:309–317 (1996). Additionally, incomplete translocations have been found to be persistent over time, and increase with high radiation LET. For instance, incomplete translocations were found not to decay in monkeys over a 30 year period; the in vitro and in vivo data showed similar incomplete translocation frequencies. Lucas, J. N., et al., *Stability of the translocation frequency following whole-body irradiation measured in rhesus monkeys*, Int'l. J. Radiat. Biol., 70:309–317 (1996).

A further physical explanation for the observed correlation between high and low LET radiation and aberration frequencies is the large difference in energy-deposition patterns produced by high- and low-LET radiation, although the correctness of this theory is not necessary for the practice of the invention. For a given dose, high-LET radiation probably produces relatively more densely packed DSBs than does low-LET. The chance of producing an incomplete chromosome exchange seemingly increases as the density of DSBs increases within an exchange site, because the more densely packed the DSBs the more potentially likely the probability of incorrect and incomplete rejoining.

Alternatively, a similar radiation signature might result based on the differential size distribution generated by DSBs from low- and high-LET radiation, respectively. High-LET produces effectively more smaller chromosome pieces compared to low-LET radiation, which might account for an increase in terminal pieces too small for translocation to be detected. The small translocations might appear as an incomplete.

Also provided according to the present invention are kits for determining the clastogenic signature of a sample of cells. Such kits may include reagents for detecting different chromosome aberrations such as hybridization probes, detectable markers, buffers, functionalized microbeads, etc. The kits may also include mechanisms for comparing the number of a first type of chromosome aberration to a second type of chromosome aberration, for example, the number of incomplete chromosome aberrations to complete chromosome aberrations. Such mechanisms include, but are not limited to, computers, software, mechanical comparators, and equivalents thereof.

5. Specific Painting Probes for Performing Chromosome Painting

Chromosome painting utilizes a group of hybridization probes which hybridize to different sections of a particular chromosome. These probes are commonly referred to as "painting probes" because they hybridize along the entire chromosome and thus cause detectable markers to be spread across the entire chromosome.

Conventional painting probes are not completely specific to particular chromosome. Rather, conventional painting probes are a mixture of probes having a varying degree of specificity for a particular chromosome. In other terms, conventional painting probes include a fraction of probes which exhibit some degree of non-specific binding to a non-target chromosome, i.e., they preferentially hybridize to a particular chromosome but also tend to hybridize to other chromosomes. The use of painting probes which do not selectively hybridize to a single chromosome introduces noise into the painting assay. As the level of non-specific hybridization among the painting probes increases, the level of noise also increases. In chromosome painting assays, it is desirable to minimize the degree of non-specific hybridization by the painting probes in order to reduce Background noise.

One way to reduce the amount of noise in chromosome painting assays is through the use of "blocking DNA." Blocking DNA refers to a library of denatured and digested unlabeled chromosomal DNA. Blocking DNA is used to compete with painting probes for hybridization to chromosomal DNA in the sample. Through this competition, blocking DNA reduces the frequency with which chromosome painting probes non-specifically hybridize to chromosomes other than the target chromosome to which the painting probe is designed to hybridize. As a result, the amount of noise due to the painting probes hybridizing to non-target chromosomal DNA is reduced. While the use of blocking DNA reduces noise in the assay to some degree, a substantial amount of noise can nonetheless be present.

Provided herein is a method for selecting a subset of probes from a sample of painting probes which exhibit a higher degree of hybridization selectivity toward the target sequence and thus a significantly lower degree of non-specific hybridization to chromosomes. This subset of probes is referred to herein as "specific painting probes" due to their ability to selectively hybridize to a particular chromosome. Use of specific painting probes in a chromosome painting assay result in the assay having substantially less noise due to non-specific hybridization to more than one chromosome.

The painting probes used in the method can be obtained either commercially or through procedures known to one of skill in the art, such as restricting and denaturing samples of the type of chromosome that is desired to be painted. The painting probes may be labeled with a detectable marker for the purpose of identifying the painted chromosome after the painting probe has been hybridized to the chromosome. Suitable detectible markers are generally disclosed in U.S. patent application Ser. Nos 08/384,497, filed Feb. 6, 1995, and 08/703,302, filed Aug. 26, 1996. The labeling may take place before, after or during the practice of the present invention.

FIGS. 4A–4D illustrates steps in a method for isolating specific painting probes. First, a sample of target chromosomes are prepared. These chromosomes are then hybridized in suspension to a set of biotin labeled painting probes in the presence of blocking DNA under hybridization conditions optimal for maximum hybridization specificity. The hybridization of chromosomes in suspension is described in U.S. patent application Ser. Nos. 08/384,497, filed Feb. 6, 1995, and 08/703,302, filed Aug. 26, 1996. An embodiment of the method for hybridizing chromosomes in suspension is also provided in the examples. The hybridization may be on glass slides or in suspension.

Figure 4A:
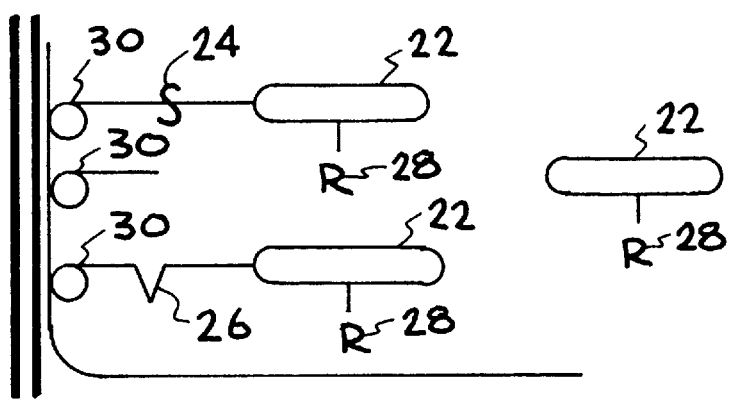
FIGS. 4A–4D illustrate the process of obtaining painting probes using blocking DNA.

As illustrated in FIG. 4A, after hybridization, the chromosomes 22 will have painting probes that specifically hybridized to them 24, painting probes that non-specificallyi hybridized to them 26, and blocking DNA hybridized to them 28.

After hybridization the chromosomes are washed to remove unhybridized probe. An exemplary washing procedure is set forth in Example 1.

The washing process removes any excess painting probes and blocking DNA, but leaves a sufficiently large number of hybridized chromosomes in suspension for analysis which have attached painting probes which specifically hybridize to the target chromosome, painting probes which nonspecifically hybridize to the target chromosome, and blocking DNA. Also present are non-hybridized chromosomes.

The hybridized chromosomes suspension are then mixed with magnetic avidin-coated microbeads 30 (hereinafter referred to as microbeads). The microbeads are complexed to the biotin-labeled painting probes 24, 26 hybridized to the chromosomes. After incubation time of 30 minutes, a magnetic field is applied which attracts the magnetic microbeads 28 that are attached to the hybridized chromosomes (FIG. 4A). Any unhybridized chromosomes remain in solution. The trapped chromosomes 22 are gently washed twice to remove any unhybridized chromosomes and debris.

The reaction mixture is then heated to 70° C. to dehybridize the painting probes and blocking DNA from the chromosomes as well as separate the beads from the probe. Once dehybridized, the painting probes are isolated from the chromosomes and microbeads.

Figure 4B:
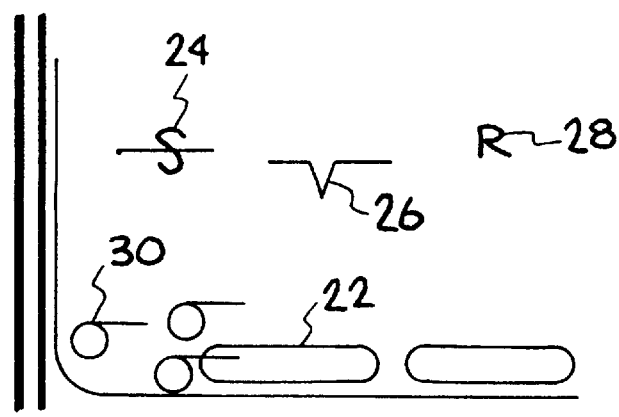

Separation of the probes may be performed by centrifuging the sample to separate the chromosomes and microbeads from the probes which remains in solution, as illustrated in FIG. 4B. The supernatant contains the probes and may be pipetted into another tube leaving the microbeads and chromosomes behind.

Figure 4C:
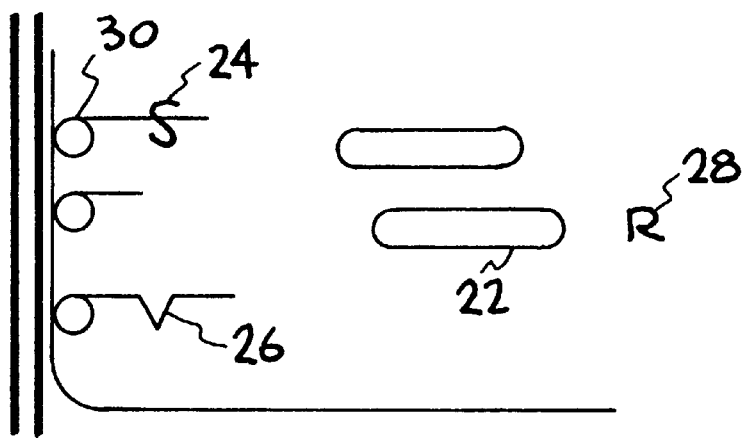

Alternatively, separation of the probes may be performed by incubating the sample at 37° C. for 1 hour with microbeads: This allows the beads to complex with the painting probes, as illustrated in FIG. 4C. Alternatively, after heat separation, the solution may be allowed to incubate at 37° C. for 1 hour. This will allow reassociation of the microbeads with the painting probes, but will not be enough time for the chromosomes to rehybridize to the painting probes. The painting probes are then trapped on a solid support and the chromosomes are discarded with the supernatant during several washes. The microbeads are then separated from the probe by heat and trapped. The solution containing only the specific painting probes is reclaimed.

The specific painting probes isolated by either of the above separation methods can be amplified by PCR in order to produce additional probes.

The specific painting probes isolated as described above may be further purified by repeating the above method using the isolated probes as the starting material in the first step of the purification process.

Figure 4D:
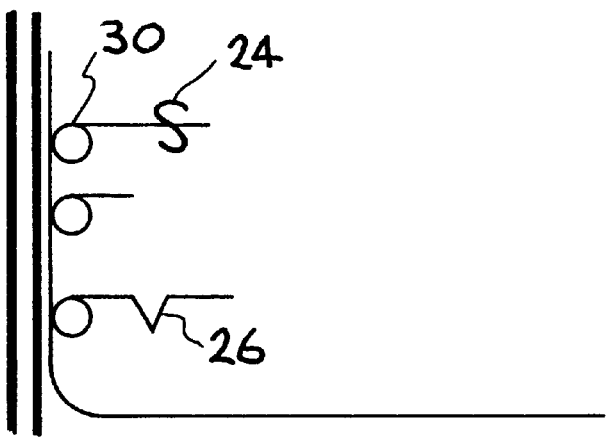

After performing the method described with regard to FIG. 4A–4D, the specific painting probes that remain are substantially specific to the target chromosome and bind to non-target chromosomes to a small degree. The specificity of the probes can be increased with additional iterations of the method. While repeating the method does tend to remove contaminants, reasonably significant amounts of non-specific painting probes will remain in the final product, as illustrated in FIG. 4D.

6. Isolation of Specific Painting Probes Using Unique Probes

Figure 5A:
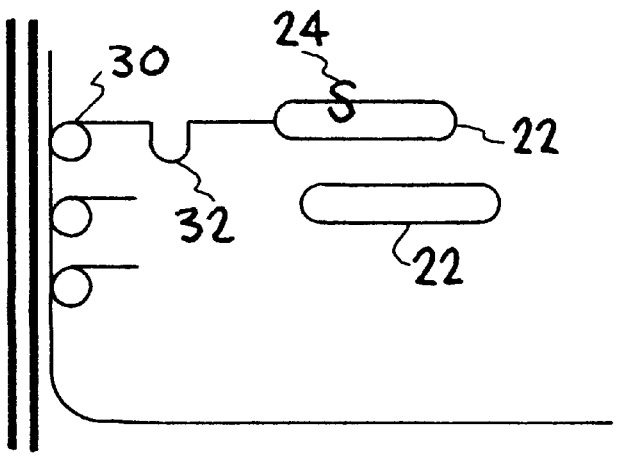
FIGS. 5A–5C illustrate the process of obtaining painting probes using a unique probe.
Figure 5B:
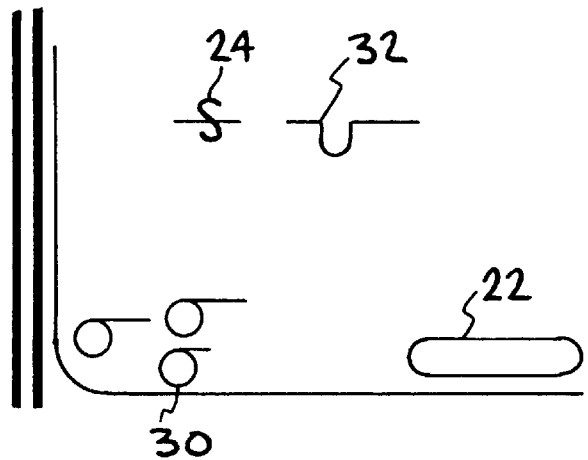
Figure 5C:
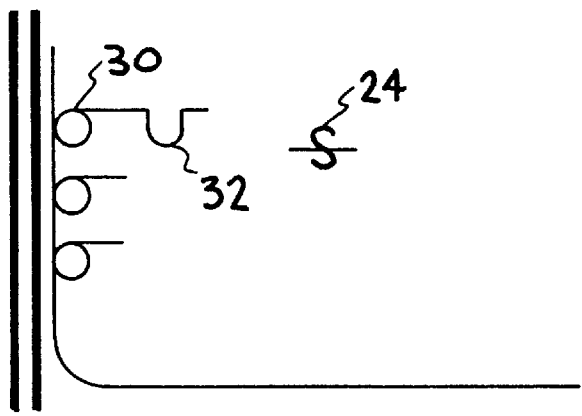

One method for further reducing the amount of noise produced by the presence of non-specific painting probes is through the use of unique probes to isolate specific painting probes, as illustrated in FIGS. 5A–5C. Unique probes refer to probes which are complementary to a short stretch of chromosomal DNA or a particular gene on a target chromosome. As a result, unique probes hybridize highly selectively to the target sequence. Because unique probes only hybridize to a very short portion of a chromosome, unique probes do not paint a chromosome and thus are not useful as painting probes.

A first step in obtaining specific painting probes using unique probes is to hybridize a sample containing chromosomes in suspension with two sets of probes: a labeled unique probe which is specific for a target chromosome and a set of painting probes. Such unique probes are available from commercial suppliers (such as Oncor), or can be generated from a DNA sequence of interest using PCR amplification, as is well understood by one of ordinary skill.

The chromosomes and the probes are hybridized under hybridization conditions generally optimized for maximum specificity. Useful techniques are generally disclosed in U.S. patent application Ser. Nos. 08/384,497, filed Feb. 6, 1995, and 08/703,302, filed Aug. 26, 1996.

As illustrated in FIG. 5A, the unique probe 32 hybridizes to the target chromosome 22. Meanwhile the unique probe 32 is immobilized using microbeads 30, thereby immobilizing the target chromosome 22. Painting probes which hybridize to the target chromosome are also immobilized by the unique probe. Immobilization of the hybridized chromosomes may be performed as described with regard to FIG. 4A. Any unhybridized chromosomes 22 may be pipetted off during washing, leaving primarily only the immobilized target chromosome 22. After washing, the sample containing the immobilized target chromosomes 22 is heated to release the unique prove 32 and painting probes 24. After heat releasing, the sample contains target chromosomes 22, microbeads 30, unique probes 32, and painting probes 24, as illustrated in FIG. 5B. The microbeads 30 (end chromosomes 22 can be separated from the unique probe 32 and painting probes 24 by centrifugation, with the probes present in the supernatant, as illustrated in FIG. 5B. The unique probe 32 can then be trapped again using the microbeads 30, thereby leaving th(e specific painting probe 24 in the supernatant, as illustrated in FIG. 5C. The specific painting probe 24 may be further purified by repeating this method using the isolated specific painting probes as starting material. The isolated specific painting probes can also be amplified using PCR, if desired.

The methods, reagents and kits of the present invention will now be described with regard to the following examples. Further objectives and advantages other than those set forth above will become apparent from the examples and accompanying drawings.

EXAMPLES

1. Hybridization of Chromosomes in Suspension Method.

This example provides a method for hybridizing chromosomes in suspension as well as a method for washing chromosomes. First, a volume of isolated chromosomes which contained $15 \times 10^5$ to $30 \times 10^5$ chromosomes is pipetted into a tube (Falcon tube No. 2054). The "fix" solution (3:1=methanol: acidec acid) has been added to chromosomes sample directly (the volum of the fix solution is between 100 and 500 microliters). After 10 minutes, the fix solution is removed by centrifugation (350 G, 10 min), and chromosome pellet was resuspended in 160 µl prewarmed hybridization mixture (40% deionized formamid, 4× SSC, 2× Denhardt's solution). 0.36 µg/20 ml biotinylated human genomic DNA probe, 0.27 µg/15 µl directly labeled human centromere DNA probe and 5.3 µl (1 mg/ml) hamster Cot-1 (GIBCO BRL, Lot No. CPP110) are added to hybridization mixture. After mixing well by tapping against the tubes, the chromosomes are denatured for 5 minutesto at 73° C. water bath, then put in ice for 5 min. The chromosomes are hybridized overnight at 43° C. in a shaking water bath. Before the washing procedure started, 200 μl 2× SSC was added into the hybridization mixture, the chromosomes were pelleted by centrifugation at 350 g for 10 minutes, washed in 500 μl prewarmed washing solution I [2× SSC, 500 μg/ml Bovine serum albumin (Amersham LIfe Science Inc. RPN 412), 5 mM EDTA] for 25 minutes at 43° C. in a shaking water bath. After another centrifugation, the chromosomes are resuspended in washing solution II (0.1× SSC, 500 μg/ml BSA, 5 mM EDTA) and passed through a second wash procedure at 43° C. for 25 minutes in a shaking water bath. The washing solution is removed by centrifugation at 350 g for 10 minutes. The hybridizaed chromosomes are ready for detection.

2. Detection of Pericentric Inversions

The probes used in this example included subcentromic DNA probe for chromosome 1 complementary to sequence region 1q12 (pUC 1.77); telomeric DNA probe for chromosome 1 complementary to region 1 p36.3 (Oncor); and pan-centromeric probe (Lucas, et al., *Rapid translocation frequency analysis in humans decades after exposure to ionizing radiation*, Int'l. J. Radiat. Biol., 62:53–63 (1992). The subcentromic probe (pUC 1.77) was labeled with digoxigenin-11-dUTP (available from Boehringer Mannheim) by nick translation. The telomeric probe (1p36.3, obtainable from Oncor) was labeled with digoxigenin. The DNA from a pan-centromeric probe was generated by amplification of genomic DNA using polymerase chain reaction (PCR) with degenerative alpha satellite primers (Lucas, et al., *Rapid translocation frequency analysis in humans decades after exposure to ionizing radiation*, Int'l. J. Radiat. Biol., 62:53–63 (1992), and was labeled with biotin-14-dCTP (Sigma) in a second round of amplification.

The chromosomes analyzed in this example were obtained from 2.9 Gy $^{60}$Co-γ-irradiated human lymphocytes according to the method described in Lucas, et al. *Rapid determination of human chromosome translocation frequency using a pair of chromosome-specific DNA probes*, Int'l. J. Radiat. Biol., 56:35–44 (1989).

Hybridization of the telomeric, subcentromic, and pan-centromeric probes to the chromosomes was performed in a manner similar to that described in Lucas, et al. *Rapid determination of human chromosome translocation frequency using a pair of chromosome-specific DNA probes*, Int'l. J. Radiat. Biol., 56:35–44 (1989). Briefly, one mL of each probe (1p36.3, 1q12 and pan-centromere) was mixed with 7 mL of hybridization buffer (final concentration of hybridization buffer in the hybridization reaction consisted of 50% formamide, 2× SSC [SSC is 0.15 M NaCl/0.01 5M Na Citrate, pH 7], 10% dextran sulfate), and hybridized overnight. The bound probes were detected by staining with anti-digoxigenin-fluorescein (Boehringer Mannheim) and avidin-Texas Red (Vector). The slides were then counterstained blue with 4,6-diamidino-2-phenylindole (DAPI).

3. Calculation of Genomic Pericentric Inversion Frequency

The measured pericentric inversions, $p_i$, involving the ith chromosome are proportional to the product of the long ($L_i$) and short arms ($S_i$) of the ith chromosome. The total genomic number of pericentric inversions, P, is obtain(ed similarly from the ratio of the sum of products of the long and short arms for the total genome to the product of the long and short arms of the ith chromosome, times the measured pericentric inversions, $p_i$, involving the ith chromosome:

$$P = p_i \sum_{j=1}^{46} (L_j S_j) / L_i S_i, \qquad (1)$$

Savage, et al., Mutation Research, 95:7–18 (1982); Hlatky, et al., Radiation Research, 129:304–308 (1992). The values for $L_i$ and $S_i$ were obtained from Morton, Proceedings of the National Academy of Sciences (USA), 88:7474–7476 (1991).

Equation (1) holds for any one of the 46 chromosomes. To apply equation (1) in this example, an extra factor of 2 is required to cover the two indistinguishable homologues of chromosome 1. For chromosome 1, the following equation was used $$2L_1 S_1 \bigg/ \left( \sum_{j=1}^{46} (L_j S_j) \right) = 2 * 7.54\% = 15.08\%. \qquad (2)$$

4. Calculation of Pericentric Inversions From G-banding Data

In practice, FISH detects pericentric inversions on only a few chromosomes at a time. From Equation (1), the inversion frequency depends on the chromosome arm size and centromere position. Ideally, one would like to scale up to the full genome from measurements made on any chromosome(s). To show the utility of Equation (1) in calculating genomic pericentric inversion frequencies, a special example involving G-banding data for 38 A-bomb survivors was used. Sachs, et al., Radiation Research, 133:345–350 (1993). A total of 102 pericentric inversions was observed, and general agreement with equation (1) was found. See Sachs, et al., Radiation Research, 133:345–350 (1993).

5. Genomic Translocation Frequency

Identification and scoring of chromosome exchange aberrations was performed using FISH as described in Lucas, et al., *Rapid translocation frequency analysis in humans decades after exposure to ionizing radiationi*, Int'l. J. Radiat. Biol., 62:53–63 (1992). The scoring criteria used (apparently site exchange-type painting pattern) was equivalent to those described in Simpson, et al. *Estimating the true frequency of X-ray-induced complex chromosome exchanges using fluorescence in situ hybridization*, Int'l. J. Radiat. Biol., 67:37–45 (1995). Only apparently simple translocatiois (AST's) and dicentrics (ASD's) were used to calculate F ratios because equality for translocations and dicentrics has been shown only for AST's and ASD's mathematically (Lucas, et al., Int'l. J. Radiat. Biol., 639:145–153 (1996) and experimentally (Simpson, et al., Int'l. J. Radiat. Biol., 67:37–45 (1995); Kovacs et al., Radiation Research, 137:3443. (1994)The translocation frequency measured by FISH was scaled to full-genome equivalents using the formula in Lucas, et al., Int'l. J. Radiat. Biol., 62:53–63 (1992), herein by reference. In brief, the formula relates the translocation frequency measured by FISH, $F_p$, to the genomic translocation frequencies, $F_G$, through the fraction of the genome covered by the probes, $f_p$, as follows:

$$F_G = F_p / (2.05 f_p (1 - f_p)) \qquad (3)$$

where the genomic conversion factor for chromosome 1 in Equation (3) is 0.156.

6. Determination of Pericentric Inversion Frequencies

After hybridization overnight and staining, the pan-centromeric probe fluoresced the centromeres red (R).

Figure 6:
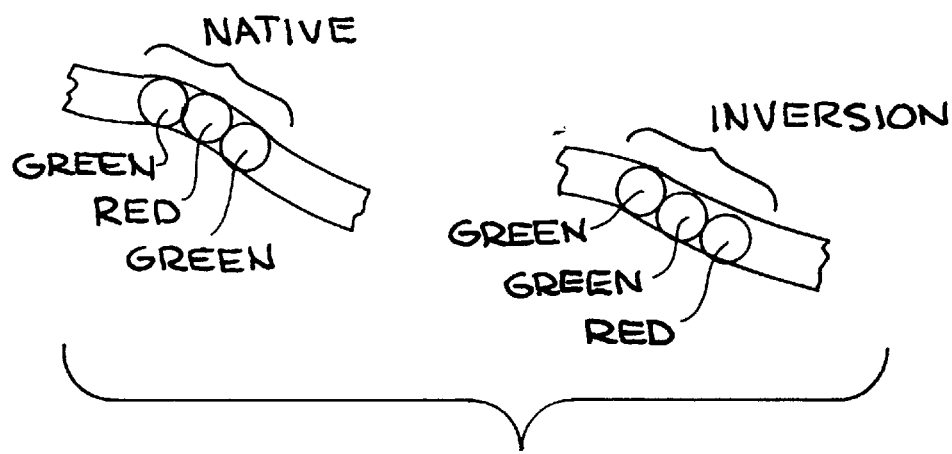
FIG. 6 illustrates a fluorescence pattern containing pericentric inversions and native chromosomes.

Meanwhile, the subcentromeric and telomere probes fluoresced the heterochromatic and telomeric regions of chromosome 1 green (G). Pericentric inversions (short arrow) and native chromosomes (long arrow) were easily recognized and distinguished based on the fluorescent pattern of the probes hybridized to the chromosome, as shown in FIG. 6 (GGR-inversion; GRG-native) short arrow The utility of the method of this invention for assessing the frequencies of pericentric inversions involving human chromosome I was evaluated by applying it to the analysis of metaphase spreads from low-LET irradiated human cells. The method facilitated fast, accurate detection of pericentric inversions and centric rings.

The observed pericentric inversions and centric rings along with the respective F ratio measured in $^{60}$Co γ-irradiated human lymphocytes are presented in Table 1. In 1966 metaphases, 24 pericentric inversions and 21 centric rings involving chromosome I were observed. Total genomic frequencies were calculated for pericentric inversion and centric rings using Equation (1). As expected, the frequency of pericentric inversions was not significantly different from that for centric rings with acentric fragments (p=0.39). This equality is comparable to the equality of inversions and interstitial deletions plus centric rings. Muhlmann-Diaz, et al., Radiation Research, 143:175–180 (1995).

The frequency of AST's and ASD's were obtained in separate, parallel experiments using the same slide sets employed here. Whole chromosome painting with a pan-centromere probe was employed according to Lucas, et al., Int'l. J. Radiat. Biol., 62:53–63 (1992). A total of 140 AST's and 142 ASD's involving chromosome 1 were detected in 1966 metaphases. Total genomic frequencies were obtained using Equation (2).

The F ratios in Table 2 were calculated as ratios of the frequency of AST's to that of pericentric inversions, and similarly for ASD's to centric rings. The F ratio was 5.6 for the ratio of the frequency of AST's to that of pericentric inversions, and it was 6.5 for the ratio of the frequency of ASD's to that of centric rings. The F ratios obtained here were in good agreement with the F ratio of 6.0 calculated based on chromosome 1 ASD and centric ring 4-Gy-x-rays data. See Griffin, et al., Int'l. J. Radiat. Biol., 67:431–439 (1995); Simpson, et al., *Estimating the true frequency of X-ray-induced complex chromosome exchanges using fluorescence in situ hybridization*, Int'l. J. Radiat. Biol., 67:37–45 (1995). This value is also in good agreement with the 6.4 value from a Monte Carlo simulation model for dicentrics and centric rings in a previous FISH study. Chen, et al., Int'l. J. Radiat. Biol., 69:411–420 (1996).

The experimental F ratios of 5.6 and 6.5 obtained in this example, and 6.0 based on FISH data of Simpson, et al., (1995) for low-LET radiation are significantly lower then the F ratio of 15 estimated from conventional staining experiments by Hlatky et al. (1992) and by Brenner (1996). However, the F ratio is not significantly different from that of 6.2 obtained by G-banding study on Hiroshima A-bomb survivors Sachs, et al., 1993. Brenner (1996) considered the low F ratio observed in Hiroshima A-bomb survivors as evidence that the majority of biological damage was caused by neutrons, not photons. However, the F ratios reported in this example indicate that such discrimination may not be valid. A clearer discrimination is obtained using the S ratio, i.e., the ratio between complete translocations and incomplete translocations, as discussed above.

TABLE 2

Chromosome aberration* measured by FISH in 2.89 Gy $^{60}$Co-γ-irradiated lymphocytes

| Number of cells | 1966 |
|---|---|
| Pericentric inversions (chromosome 1) | 24 |
| Pericentric inversions / cell | 0.081 ± 0.017 |
| Centric rings (chromosome 1) | 21 |
| Centric rings / cell | 0.071 ± 0.016 |
| AS Translocations (chromosome 1) | 140 |
| AS Translocations / cell | 0.46 ± 0.04 |
| AS Dicentrics (chromosome 1) | 142 |
| AS Dicentrics / cell | 0.46 ± 0.04 |
| AS Translocations / pericentric inversions | 5.6 + 2.1, −1.4 |
| AS Dicentrics / centric rings | 6.5 + 2.5, −1.6 |

*After 2.89 Gy $^{60}$Co-γ irradiation, 1966 metaphase lymphocytes are scored in 2 separate studies. The first one measure the intra-chromosome 1 aberration. The second one measure apparently simple (AS) translocation and dicentrics using whole chromosome painting on chromosome 1 with a pan-centromeric probe. To convert the chromosome 1 aberration to whole genomic equivalent, the factor for pericentric inversion (or centric ring) is 0.1508 (see Equation 1); for translocations #or dicentrics is 0.1560 (see Equation 2).

7. Detection of Clastogenic Signature For $^{60}$Co And $^{137}$Cs gamma rays

Cells were irradiated with $^{60}$Co and $^{137}$Cs gamma rays in order to produce aberrations and detect thE frequency of their occurance. Irradiation of cells with $^{60}$Co and $^{137}$Cs gamma rays has been described elsewhere. Lucas, J. N., et al., *Rapid determination of human chromosome translocation frequency using a pair of chromosome-specific DNA probes*, Int'l. J. Radiat. Biol., 56:35–44 (1989). For carbon ion irradiation, whole blood was exposed to 290 MeV/n carbon ions attenuated by a 146 mm water column. The blood sample was loaded in a 1 mm thick plastic holder. The track-average LET (including the fragments) was 77 keV/mm. All samples were set in culture following exposure in RPMI medium supplemented with serum and PHA.

Cultures were terminated after 48 h plus 4 h incubation in 0.2 mg/ml colcemid. The average dose was 3.0 Gy. For $^{56}$Fe ion irradiation, whole blood was exposed to 1 GeV/n iron ions at Brookhaven National Laboratory. The track-average LET (including the fragments) was about 140 keV/micron. Cells were incubated as above. The average dose was 3.0 Gy. For tritium exposure, lymphocytes were irradiated; the average dose was 0.6 Gy.

Except where noted, all data analyzed were obtained using FISH. Identification and scoring of chromosome exchange aberrations using chromosome painting to generate additional data employed the methods of J. M. Lucas, et al., *Rapid translocation frequency analysis in humans decades after exposure to ionizing radiation*, Int'l. J. Radiat. Biol. 62:53 (1992). The chromosome exchange aberrations scored here were apparently simple (AS) exchange-type painting patterns. Simpson, P. J. and Savage, J. R. K., *Estimating the true frequency of X-ray-induced complex chromosome exchanges using fluorescence in situ hybridization*, Int'l. J. Radiat. Biol., (37:37–45 (1995).

The pattern resembles that of translocations. An incomplete apparently simple (AS) translocation pattern resembles that of an incomplete reciprocal translocation where the solid painted fragment contains one centromere. These aberrations are those translocations where reciprocity of the exchange event is not registered, either because the exchanged is actually incomplete, or because one of the exchanges segments involves the extreme, unpainted, terminal part of the arm.

Figure 7A:
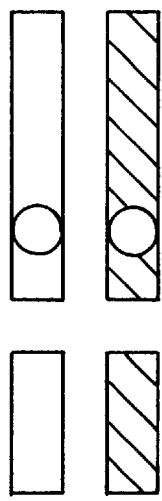
FIG. 7A illustrates an unpainted chromosome (clear) and a painted chromosome (solid).
Figure 7B:
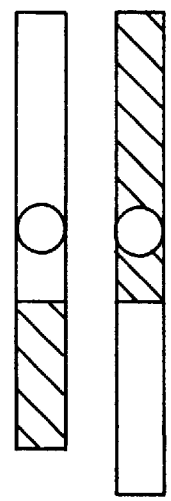
FIG. 7B illustrate painted chromosomes having an apparently simple translocation.
Figure 7C:
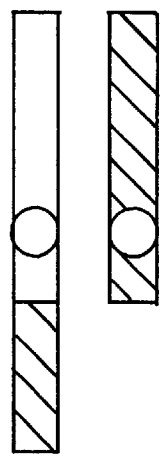
FIGS. 7C and 7D illustrate painted chromosomes having two types of incomplete translocations.
Figure 7D:
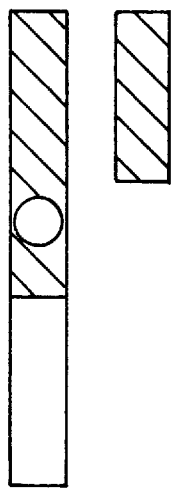
Figure 7E:
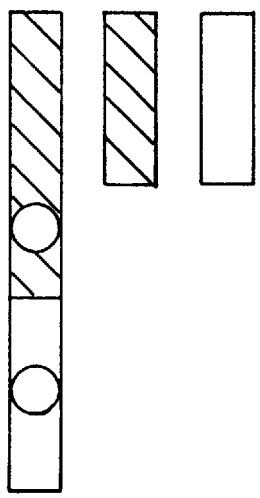
FIG. 7E is a representation ol painted chromosomes having a dicentric and a fragment.
Figure 7F:
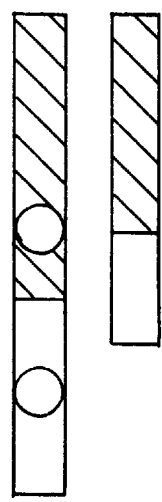
FIG. 7F is a representation of painted chromosomes having a reciprocal dicentric translocation.

FIG. 7A is a representation of an unpainted chromosome (clear) and a painted chromosome (solid). An apparently simple translocation is depicted in FIG. 7B, where a painted and an unpainted chromosome misrejoin after receiving one DBS on each chromosome. Incomplete apparently simple translocations were recognized as bicolor chromosome derivatives, where the centromere resides on the unpainted segment. The other chromosome derivative is painted and has a centromere, but has no unpainted segment attached, as depicted in FIG. 7C. Other types of incomplete aberrations exist, such as the incomplete illustrated ir FIG. 7D, but are more difficult to recognize. Other types of incomplete aberrations which exist include a dicentric and a fragment, illustrated in FIG. 7E, and a reciprocal dicentric translocation, illustrated in FIG. 7F.

Photomicrographs from previous data which contained enough incompletes to be statistically significant were rescored Where possible, data were combined, and in some cases, additional scoring was performed to improve statistics. The blind scoring of coded photomicrographs was performed by technicians unfamiliar with the project goal. Photomicrographs were either reanalyzed from previous studies, or new photomicrographs were analyzed for this study.

The significance estimate for testing the equality of S-ratios between any two populations compared here was calculated by a likelihood ratio test using a Generalized Linear Model (GLM) on two nested hypotheses. The four outcomes were assumed to be distributed as independent Poisson random variates with a logarithmic link function. The null hypothesis included terms for offset, population and outcome type. The alternative included an additional interaction term. The models were fit and tested using S-PLUS version 3.4 (Mathsoft, Inc., Seattle Wash., 1995).

8. In vitro S Ratio Measurements For $^{60}Co$, $^{137}Cs$, $^{56}Fe$ and $^{12}C$ In vitro S ratios were measured for four different radiations ranging from low- to high-LET. Table 1, below, shows the in vitro S ratios measured for $^{60}Co$ and $^{137}Cs$ gamma rays and for $^{56}Fe$ and $^{12}C$ ions, together with calculated values for 220- and 250-kV X rays from published data by other laboratories. Knehr, S., et al., *Chromosome analysis by fluorescence in situ hybridization: further indications for a non-DNA-proportional involvement of single chromosomes in radiation-induced structural aberrations*, Int'l J. Radiat. Biol., 70:385–392 (1992); Stephan, G., and Pressl, S., *Chromosome aberrations in human lymphocytes analyzed by fluorescence in situ hybridization after in vitro irradiation, and in radiation workers, 11 years after an accidental radiation exposure*, Int'l. J. Radiat. Biol., 71:293–299 (1997).

For those data, total incompletes measured were halved for comparison with FIG. 7C. The relative biological effectiveness (RBE) for $^{137}Cs$ gamma and 220-kV X rats and for $^{56}Fe$ and $^{12}C$ ions was calculated as the ratio of the total number of chromosome translocations measured for each radiation, to that measured for $^{60}Co$ at the same dose.

As appearing in the Table 1:

"Unexposed" refers to a group of 30 unexposed healthy individuals ranging in age from 18 to 98 y (86,190 cells scored).

"Chernobyl" refers to a group of 26 Chernobyl liquidators whose chronic dose estimates ranged from 0.2 Sv to 10 Sv (5,722 cells scored).

"Tritium" refers to a tritium worker who accidentally inhaled tritium oxide in 1985 that resulted in a whole-body dose of 0.44 Sv (1,000 cells scored). We resampled this individual in 1995, 5 y after the first FISH translocation measurements in 1992. The ASTs and incompletes remain unchanged at 41 ASTs and 11 incomplete ASTs for a S ratio of 3.73+2.44, −1.31.

"Radiation worker" refers to an individual who was exposed to photons and particle radiation from high-energy accelerator operations during 30 y of work in that environment. This individual was a dosimetry expert and kept meticulous records of his exposure history.

"Nuclear dockyard worker" refers to a worker who, based on his dose badge readings and environmental monitoring data, received a dosage of about 246 mSv (gamma) plus 111 mSv (neutrons) by dosimetry experts from Leigh, Day & Co., London, U.K. His measured S ratio was 3.7 (5,825 cells scored), significantly lower than 8.23 S ratio measured in 86,190 cells for 30 unexposed individuals.

"Benzene workers" refers to 20 benzene workers with a history of benzene poisoning (18,583 cells scored).

"Monkeys" refers to measurements on monkeys presented in Lucas et al., *Stability of the translocation frequency following whole-body irradiation measured in rhesus monkeys*, Int. J. Radiat. Biol., 70:309 (1996).

"Y-12 criticality and A bomb survivors" refers to measurements presented in Lucas et al., *Rapid Translocation Frequency Analysis in Humans Decades After Exposure to Ionizing Radiation*, Int. J. Radiat. Biol., 62:53–63 (1992).

"$^{137}Cs$ (1)" refers to measurements presented in Durante, et al., *Rejoining of Radiation-induced Chromatin Breaks*, Radiation Research, 145:274–280 (1996). Data on translocations was obtained gratefully by personal communication from Dr. Durante.

"220-kV X rays" refers to measurements presented in Knehr et al., *Chromosome analysis by fluorescence in situ hybridization: further indications for a non-DNA-proportional involvement of single chromosomes in radiation-induced structural aberrations*, Int'l. J. Radiat. Biol., 71:35–39.

"250-kV X rays" refers to measurements presented in Stephan, et al., *Chromosome aberrations in human lymphocytes analyzed by fluorescence in situ hybridization after in vitro irradiation, and in radiation workers, 11 years after an accidental radiation exposure*, Int'l. J. Radiat. Biol., 71:293–299.

TABLE 1

S ratios measured by FISH in human lymphocytes after exposure to clastogenic agents.

| Exposure type | Cells | ASTs* | Inc† | ASTs/Inc (S ratio) |
|---|---|---|---|---|
| In vitro | | | | |
| Radiation exposure | | | | |
| Low-LET: $^{60}Co$ | 2,000 | 317 | 32 | 9.91 + 0.8, −1.9 |
| $^{137}Cs$ | 7,884 | 255 | 30 | 8.50 + 0.5, −1.8 |
| $^{137}Cs$ (1) | 236 | 167 | 18 | 9.28 + 3.8, −2.3 |
| 220-kV X rays | 12,618 | 919 | 88 | 10.4 + 0.3, −0.3 |
| Tritium | 5,809 | 135 | 34 | 3.97 + 1.2, −0.9 |
| High-LET: $^{56}Fe$ ions | 1,262 | 143 | 70 | 2.04 + 0.5, −0.4 |
| $^{12}C$ ions | 264 | 37 | 16 | 2.31 + 1.3, −0.8 |
| Chemical exposure | | | | |
| Bleomycin | 1800 | 49 | 21 | 2.33 + 1.1, −0.7 |

TABLE 1-continued

S ratios measured by FISH in human lymphocytes
after exposure to clastogenic agents.

| Exposure type | Cells | ASTs* | Inc† | ASTs/Inc (S ratio) |
|---|---|---|---|---|
| *In vivo* | | | | |
| Low-LET exposure | | | | |
| Unexposed | 86,190 | 362 | 44 | 8.23 + 2.0, −1.4 |
| Monkeys | 2,612 | 175 | 17 | 10.0 + 4.3, −2.6 |
| Chernobyl | 5,722 | 242 | 27 | 8.96 + 2.0, −2.6 |
| Tritium exposure | | | | |
| Tritium worker | 1,000 | 44 | 11 | 4.00 + 2.6, −1.4 |
| Mixed-LET exposure | | | | |
| Radiation worker | 3,428 | 48 | 16 | 3.00 + 1.6, −1.0 |
| Y-12 criticality | 3,143 | 133 | 43 | 3.09 + 0.9, −0.6 |
| Nuclear dockyard | 5,825 | 37 | 10 | 3.70 + 2.6, −1.3 |
| A-bomb survivors | 9,382 | 137 | 24 | 5.71 + 2.1, −1.4 |
| Chemical exposure | | | | |
| Benzene workers‡ | 18,583 | 50 | 25 | 2.00 + 0.8, −0.6 |

*Apparently simple translocations (Simpson and Savage 1995).
†Incomplete apparently simple translocations.
‡In the control group, only 2 incompletes were observed in 16 translocations.

Figure 8:
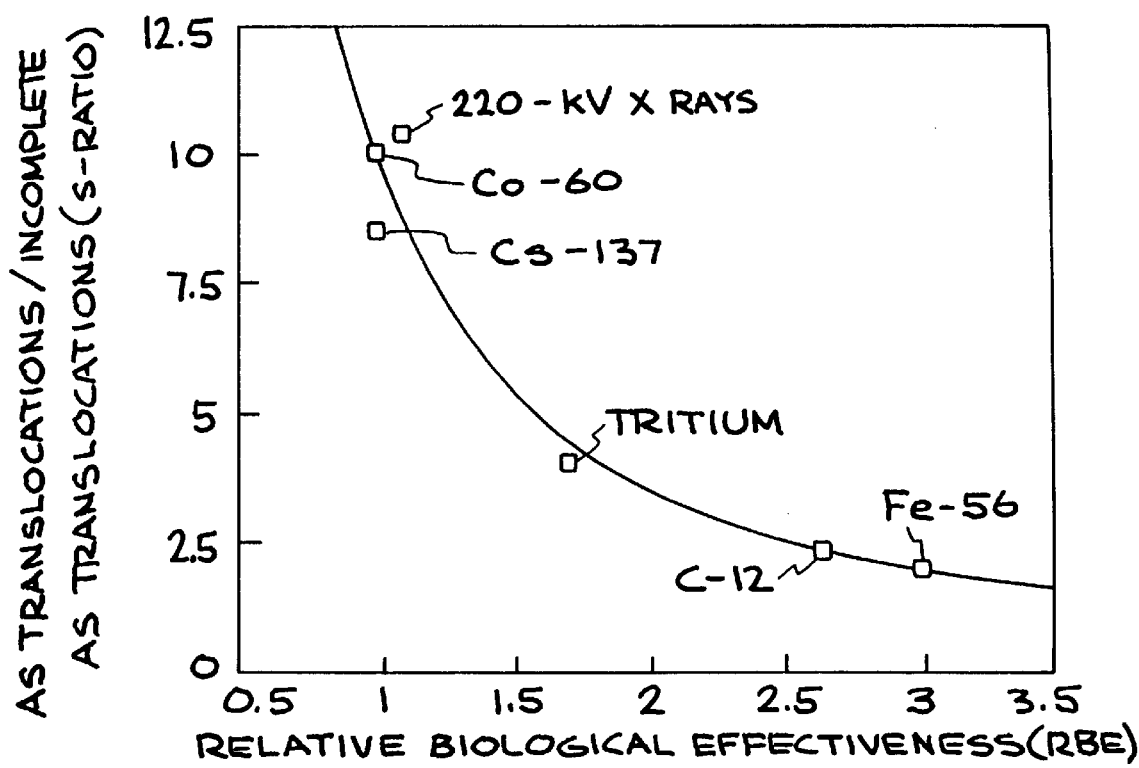
FIG. 8 illustrates a relationship between radiation RBE and the S ratio.

As can be seen from Table 1 and illustrated in FIG. 8, a clear correlation was observed experimentally between radiation RBE and S ratio. The S ratio is independent of dose, and it varies inversely with the RBE of the radiation. The low-LET radiations, having the lowest RBE, gave the highest S ratio of 10; $^{56}$Fe ion radiation, having the highest RBE, gave the smallest S ratio of 2.04; and tritium, which has an intermediate RBE, gave an S ratio of 3.8 (between the low- and high-LET radiations). Both $^{60}$Co and $^{137}$Cs have very similar RBEs and gave similar S ratios of ~10. S ratios measured for two different doses of $^{60}$Co gamma rays, 1.9 and 3.9 Gy, gave similar values of 9.1 and 10.5, respectively. Similarly, $^{56}$Fe ion doses of 0.25, 0.75, 1.25, 2.0, and 4.0 Gy gave statistically identical S ratios of ~2 for each dose.

Some published low-LET FISH data do show a low S ratio, e.g., 4.2 by Fantes et al. 1995. However, in these cases, the aberrations scored were low compared to those low-LFT data in Table 1. Although incompletes analyzed here are fromi FISH data, those measured by conventional staining appear to support the S ratio radiation signature. For example, published conventional staining data for low-LET radiation show about 10% of the aberrations are incompletes. Brewen, J. G. and Brock, R. D., *The exchange hypothesis and chromosome-type aberrations*, Mutation Research, 6:245–255 (1968).

The S ratios measured in lymphocytes of individuals exposed in the past to low- and intermediate-LET radiation were in good agreement with the S ratios calculated from that in vitro measurements (Table 1). For low-LET exposure, 30 unexposed individuals (S ratio=8.2+2.3, −1.4), 7 rhesus monkeys (exposed to 2.3-GeV protons) evaluated 30 y after exposure (S ratio=10+4.3, −2.6), and 26 Chernobyl liquidators (S ratio=9+2, −2.6), all had S ratios In excellent agreement with that measured in vitro (average in vitro S ratio was 9.5+2, −1.5).

Moreover, the S ratio of 10 calculated for 220-kV, X-ray, in vitro irradiated lymphocytes of unexposed rhesus monkeys was identical to the S ratio above for rhesus monkeys irradiated 30 y previously. In this group, the translocation frequency has been shown to remain stable since their exposure 30 y ago. Lucas, J. N., et al., *Stability of the translocation frequency following whole-body irradiation measured in rhesus monkeys*, Int'l. J. Radiat. Biol., 70:309–317 (1996). In addition, for this group, the frequency of incomplete translocations appears to be persistent as well when compared to in vitro and unexposed data. The results showed 167 translocations to 17 incompletes for monkeys exposed 30 y ago, 41 translocations to 4 incompletes for 220 KV X-ray in vitro exposed monkey lymphocytes, and 362 translocations to 44 incompletes for unexposed people, for S ratios of 10,10.3, and 8.23, respectively.

The S ratio calculated for the tritium-exposed individual (4+2.6, −1.4) agreed well with the in vitro measured tritium S ratio (4+1.2, −0.9). Additionally, this individual was resampled in 1996, 5 y after the first FISH translocation measurements in 1992. The ASTs and incompletes remain unchanged at 41 ASTs and 11 incomplete ASTs for a S ratio of 3.73+2.44, −1.31.

S ratios measured in individuals exposed to mixed high- and low-LET radiation showed values that were between that for high- and low-LET radiation (Table 1).

9. Estimation of Neutron Dosage Using S Ratio

Described in this example is the use of the S ratio to estimate the neutron dose for A-bomb survivors. The RBE for A-bomb survivors was inferred from measured S ratios for low-LET radiation. To estimate the RBE for an individual with past radiation exposure, the in vitro S ratios in FIG. 8 were fitted with a power function of the form $y=ax^b$, where y is the S ratio, x is the RBE, and a and b are constants determined from the fit to be +9.53 and −1.46, respectively. This equation was used with the in vitro derived constants, a and b, to inferred RBEs for exposed individuals in Table 1. The inferred RBE for A-bomb survivors was 1.4, higher than an RBE of 1 expected for pure gamma irradiation. In contrast, Chernobyl accident victims and rhesus monkeys (both low-LET exposures), respectively, showed an inferred RBE of 1.04 and 0.97, more consistent with pure gamma exposure. The S ratio for A-bomb survivors was significantly lower than that calculated for in vitro gamma irradiated cells (p value=0.02, Table 1). The higher RBE (lower S ratio) for A-bomb survivors suggests a sicnificant neutron component to the dose.

Figures 1D, 1E, 1F:
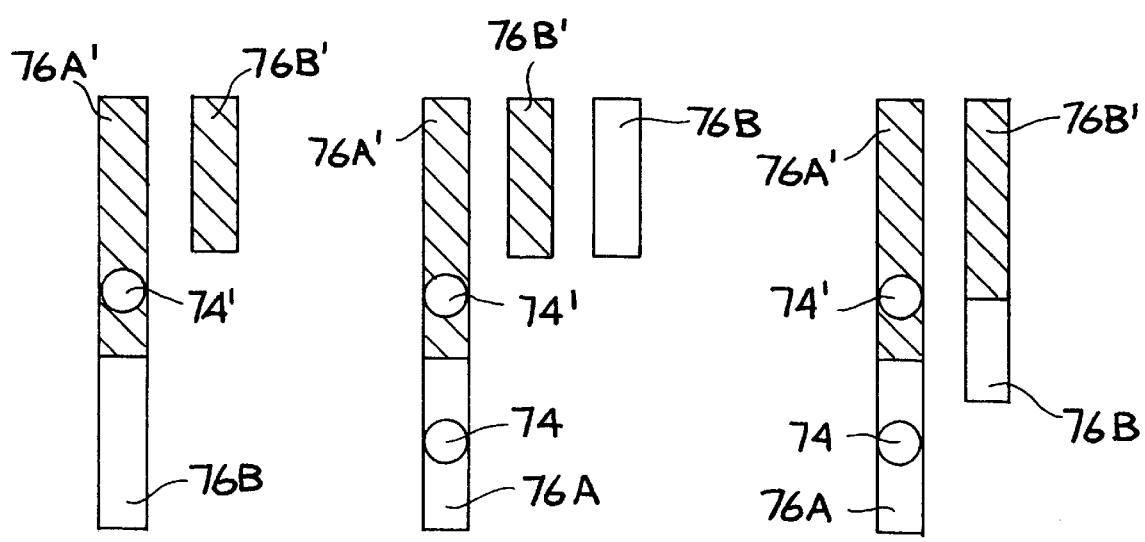

In a more extensive data set for A-bomb survivors, Kodama, Y., et al., *Estimation of minimal size of translocated chromosome segment detectable by fluorescence in situ hybridization*, Int'l. J. Radiat. Biol., 71:35–39 (1997), found an even stronger indication of a neutron contribution to dose. Assuming their "hidden reciprocals" are actually incompletes, their data shows an S ratio of 3.25 suggesting an RBE around 2 from FIG. 1. This pattern is seen also in the Y-12 criticality exposure, Lucas, J. N., et al., *The persistence of chromosome translocations in a radiation worker accidentally exposed to tritium*, Cytogenet. Cell Genet, 60:255–256 (1992), which is known to have a neutron component to the dose. In that case, the inferred RBE was 2.16 and the measured S ratio was 3.1.

10. Measuring Exposure t Bleomycin And Benzene Using a S Ratio

S ratios were also measured for two chemical exposures, bleomycin and benzene. These ratios were found to be significantly lower than those measured for low-LET radiation. Bleomycin, which is radiomimetic, Taylor, A. M. R. Progress and Topics in Cytogenetics 4, A. A. Sandberg (Alan R. Liss, Inc., New York, p. 167, 1983), was used to expose lymphocytes in vitro. The measured S ratio for bleomycin was 2.3+1.1, −0.7 (Table 1). The measured S ratio for a group of 20 workers chronically exposed to benzene was 2.0+0.9, −0.6, (Table 1). In the benzene-exposed group, 25 incomplete translocations were observed, and 50 complete translocations were found in 18,583 cells. Because the S ratio for the benzene-exposed group was significantly lower than that for the unexposed group in Table 1 (p value=$10^{-6}$), the benzene data suggest that discrimination between exposure to low-LET radiation and clastogenic (chromosome breaking) chemicals can be accomplished using S ratios, even at low doses (near background translocation frequencies) where it is difficult to discriminate between these types of exposure classes based on the translocation frequency alone.

11. Measurement of S Ratio Using Magnetic Separation of Hybridized Chromosomes in Solution This example teaches using magnetic separation techniques, such as those described above with regard to generating specific painting probes, to measure S ratios.

According to this example, a suspension of hybridized chromosomes was obtained and then washed, as described in the methods disclosed in U.S. patent application Ser. Nos. 08/384,497, filed Feb. 6, 1996, and 08/703,302, filed Aug. 26, 1997. The washing process removes the excess probes, but leaves sufficiently large numbers of hybridized chromosomes in suspension for trapping and analysis.

Figure 9A:
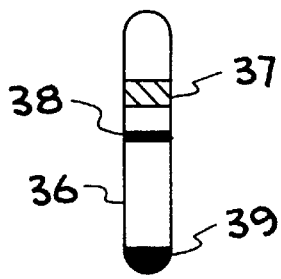
FIGS. 9A–9D illustrates different chromosomes and chromosome derivatives.

FIG. 9A shows a chromosome 36 after hybridization with probes pUC1.77 (subcentromeric region of chromosome 1) 37, pancentric (probe to all centromeres) 38, and p1.79 (probe to the telomeric region of chromosome 1) 39.

Figure 9B:
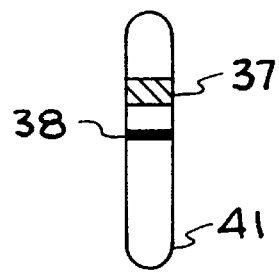

FIG. 9B shows a chromosome derivative 41 in which the telomeric region has been translocated to another chromosome in the genome. As illustrated, the telomeric probe 39 coes not hybridize to this chromosome.

Figure 9C:
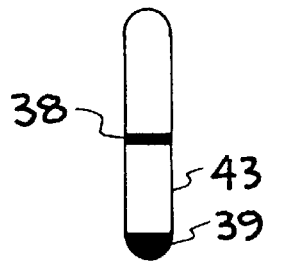

FIG. 9C shows another chromosome derivative 43 in which the subcentromeric region has been translocated to another chromosome in the genome. As illustrated, the subcentromeric probe 37 does not hybridize to this chromosome.

Figure 9D:
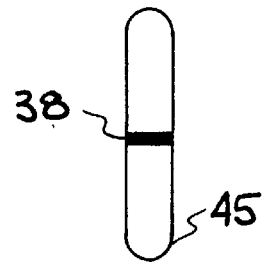

FIG. 9D shows a representation of a non-hybridized chromosome 45.

Figure 10A:
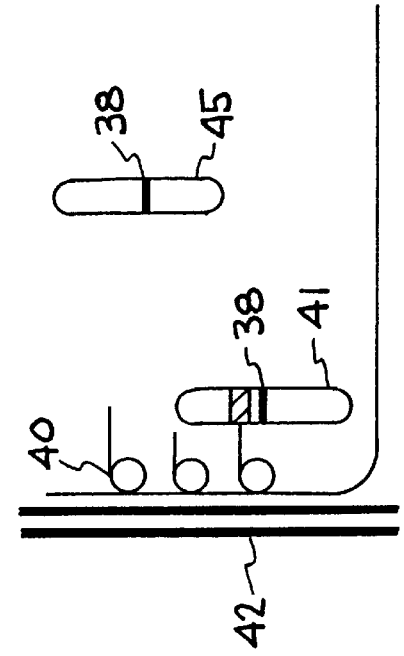
FIGS. 10A–10D illustrate separation of chromosomes using magnetic techniques.

FIG. 10A shows a method for distinguishing between chromosomes with a telomeric region (normal chromosome 36 and translocated chromosome derivative 43) and chromosomes without a telomeric region (translocated chromosome derivative 41 and nonhybridized chromosomes). As illustrated, the telomeric probe, p1.79, (39) is labeled with biotin-11 DUTP. The solution is then incubated with avidin coated magnetic beds 40 for 10 to 30 minutes, then placed in a magnetic field 42. Normal chromosome 36 and translocated chromosome derivative 43 are trapped by the magnetic field 42 via the telomeric probe 39. Meanwhile, the supernatant contains translocated chromosome derivative 41 with the pUC1.77 probe 37 hybridized and unhybridized chromosome 45.

Figure 10B:
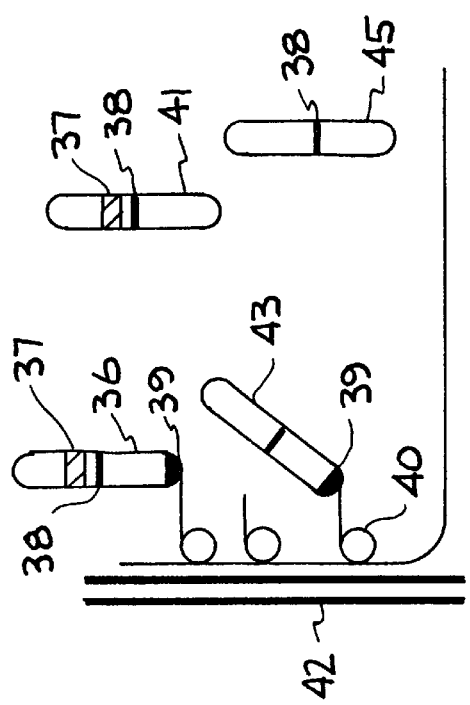

The translocation frequency can be estimated at this point as the ratio of pUC1.77 probe 37 in the supernatant to the total cells. The amount of pUC1.77 can be determined by labeling pUC1.77 with a detectable marker, such as a fluorescent reporter molecule. In addition, translocations can be trapped in a second hybridization by labeling pUC1.77 with a different attachment molecule as illustrated in FIG. 10B (or rehybridizing with biotin). The total cells can be defined as the starting material, or estimated from the total chromosomes recovered after hybridization. The total number of recovered chromosomes after hybridization can be estimated from Lucas et al., *A rapid method for measuring pericentric inversions using fluorescence in situ hybridization (FISH)*, Int'l. J. Radiat. Biol., 71:29–33.

The translocated chromosomes 41 and 43 can be released and fixed in absolute methanol:glacial acetic acid (3:1). The translocated chromosomes 41 and 43 are then dropped on glass and rehybridized to detect incomplete translocations. Using a whole chromosome 1 paint probe, all of the translocations will be bi-color, but the incomplete translocations are one solid color. Using a pantelomeric probe (probe that stains the telomeric sequence of all chromosomes), the complete translocations have probe at each terminal of the chromosome, but the incomplete translocation have probe only at the q terminal. The translocations trapping method can be repeated until all translocations have been removed from the supernatant. Because the sample in FIG. 10B contains the unhybridized chromosomes and the translocations together, the translocations frequency should be proportional or equal to this number.

Figure 10C:
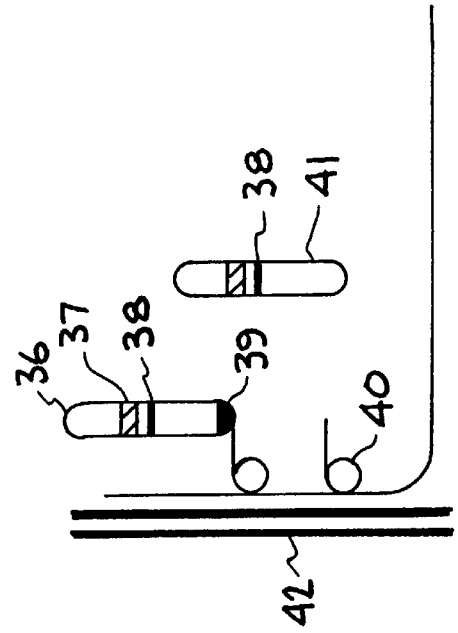
Figure 10D:
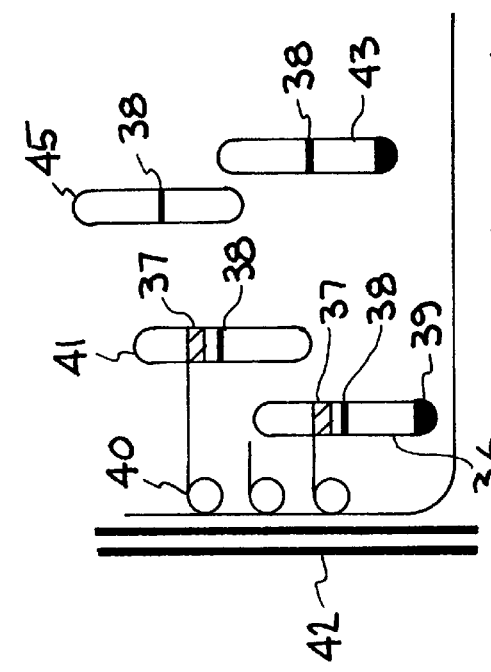

FIGS. 10C and 10D show an alternative method for separating the trapped translocations. FIG. 10C shows a method for distinguishing between chromosomes with a subcentromeric region (normal chromosome 36 and translocated chromosome derivative 41) and chromosomes without a subcentromeric region (translocated chromosome derivative 43 and nonhybridized chromosomes 45). In FIG. 10C, pUC1.77 probe 37 is labeled with biotin and is trapped. This scheme traps normal chromosome 36 and the chromosome derivative 41. The supernatant contains unhybridized chromosome 45 and the chromosome derivative 43.

In FIG. 10D, after a second hybridization with biotin-labeled p1.79 probe 39, normal chromosome 36 is trapped and the translocated chromosome 41 is in the supernatant. The number of translocations can be measured from the amount of pUC1.77 probe 37 present. The number of cells can be estimated from the amount of trapped normal chromosome 36. Again, the frequency of translocations is the ratio of trapped normal chromosomes to the translocated chromosome 41 in the supernatant. Trapped unhybridized and the translocations together, the translocations frequency should be proportional or equal to this number. The incompletes can be measured in the supernatant as described above.

It should be noted here that probes pUC1.77 and p1.79 can be replaced by any similar probes that are similarly separated relative to the centromere. The probes sequence or even specific location along the chromosome need not be known. The probes may be generated by microdissection techniques for any given chromosome(s). Generation of the region-specific probes may be achieved using chromosome microdissection techniques similar to that recently described by Guan, et al., "Generation of band-specific painting probes from a single microdissected chromosome." Hum Mol. Genet. 2: 1117–1131.(1993); and Meltzer, et al., "Rapid generation of regions specific probes by chromosome microdissection and their application." Nature Genetic 1: 24–28 (1992).

Metaphase chromosomal spreads may be stained by trypsin Giemsa banding, although unstained spreads may be used. The appropriate region of the p arm of the target chromosome is then microdissected using UV-treated microneedles attached to a micromanipulator. The resulting fragment is transferred to ai microcentrifuge tube containing a 20 ml collecting drop with 50 mg/1 of proteinase-K.

This procedure is repeated approximately 5 times to generate sufficient copies for the next PCR stage. The dissected chromatin is treated with topisomerase 1, which greatly increases the efficiency of the subsequent amplification. The PCR amplification is performed using the technique described in detail by Meltzer et al., 1992 and Guan et al., 1993. The PCR mixture is the collected drop containing the microdissected DNA fragment, 1.5 mM universal primer, 200 mM dNTP, 1 mM MgCl2, 50 mM KCl, 10 mM TrisHCl pH 8.4 0.1 mg/me gelatin, and 2.5 U Taq DNA polymerase.

12. Retrieval of Specific Painting Probes Using Blocking DNA

This example describes a method for obtaining a subset of specific painting probes from a set of painting probes. In this example, a set of painting probes is hybridized to a target chromosome in the presence of blocking DNA according to the methods disclosed in U.S. patent application Ser. Nos. 08/384,497, filed Feb. 6,1996, and 08/703,302, filed Aug. 26, 1997. The suspension is then spun down for 15 minutes at 1200 RPM. All the liquid is taken out of the tube and followed by a wash of 400 ml of 2× SSC to remove excess probe. The solution is then placed in a shaker water bath at 42° C. for 30 minutes, followed by centrifugation at 1200 RPM for 10 minutes. The supernatent is then removed, and the chromosomes are resuspended in 67.5 ml warm IBM buffer (IBM+milk, IBM being 50 mM KCl, 10 mM MgSO$_4$, and 5 mM Hepes buffer), and warmed in the water bath shaker 40–42° C. The IBM buffer and the chromosomes are mixed by flicking the tube.

Next, 7.5 ml of avidin-labeled magnetic beads (for example, BioMag Streptavidin 8-1466 OA) are added to the IBM and chromosome mixture. The amount of IBM buffer should be 9:1 of the amount of beads. This mixture is mixed by flicking the tube for a few minutes, and then is incubated for 2 hours at 37° C. The tube should be flicked again 15 minutes after the initial mixing.

After incubation, the tube containing the solution and beads are placed next to a magnet. After waiting a few minutes for the beads to move toward the magnet, the supernatent is pipetted out of the tube and discarded. The beads and chromosomes are resuspended in 300 ml 0.005% IBM without milk. The mixture is then placed in the water bath shaker and agitated for 15 minutes.

After this, the tube is placed next to the magnet again for a few minutes to allows the beads to move toward the magnet. Following this, the supernatent is pipetted out of the tube and discarded. These isolation steps are repeated twice.

Following the isolation, the beads, probe and chromosome are resuspended in 50 ml Hong's denaturing solution (70 ml hybridization mixture+30 ml H$_2$0), and denature at 72° C. for 10 min, thus promoting separation of the beads, probe and chromosomes. The tube is centrifuged and the top two-thirds of the supernatent is removed, promoting the beads and the chromosomes to go to the bottom and the probe to be at the top.

Next, 67.5 ml of warm IBM buffer (IBM+milk) is added to the probe mixture (i.e. supernatent), and then 7.5 ml of beads is added to the IBM and probe mixture. This mixture is then mixed by flicking the tube for a few minutes. Next, the solution is incubated at 37° C. for 1 hour, permitting reassociation of the beads with the probe, but generally not being long enough to permit rehybridization of the chromosomes.

After incubation, the solution is placed next to a magnet, thus separating the probe and beads from the chromosomes that remain in solution. The chromosomes are pipetted off, and may be saved to run on a gel. The beads and probe are resuspended in 400 ml H$_2$O and are transferred to a PCR tube. The tube is then placed next to a magnet to pull the beads and probe to the end of the tube. Following this, the water is then pipetted off and discarded. The beads and probe are resuspended in 50 ml of H$_2$O, and the suspension is heated at 100° C. for 5 min, thus promoting separation of the probe and beads. The solution is then cooled on ice for 5 minutes, and is then placed next to a magnet to separate the beads. The supernatent is highly enriched in the desired specific painting probe, and can be used in PCR amplification.

13. Retrieval of Specific Painting Probes From Hybridized Chromosomes on Glass Slide The procedures followed are similar in spirit to Example 12 are used, except that the chromosomes are hybridized to the probes on a glass slide. Following hybridization, the slide is heated at 95° C. in 50 ml of water for 5 min to remove the probe 10 ml of labeled magnetic beads are added to the water and bead mixture, and this mixture is incubated for 1–2 hours at 37° C., while being shaken. The mixture is then placed next to a magnet, and the supernatent containing the specific painting probe removed. This supernatent can be amplified using PCR.

While the present invention is disclosed by reference to the preferred embodiments and examples detailed above, it is to be understood that these examples are intended in an i lustrative rather than limiting sense, as it is contemplated that modifications will readily occur to those skilled in the art, which modifications will be within the spirit of the invention and the scope of the appended claims. All of the patents, patent applications, and publications cited in this application are intended to be incorporated herein by reference.

What is claimed is:

1. A method for detecting a pericentric inversion in a chromosome having a telomeric region, a subcentromeric region and a centromeric region comprising:

contacting a first probe having a sequence capable of selectively hybridizing to the telomeric region, a second probe having a sequence capable of selectively hybridizing to the subcentromeric region, and a third probe capable of selectively hybridizing to the centromeric region with the chromosome such that the first, second and third probes hybridize to the chromosome;

determining a relative positioning of the first, second and third probes when hybridized to the chromosome; and detecting a pericentric inversion based on the relative positioning of the first, second and third probes.

2. The method according to claim 1 wherein the telomeric region occurs on a first side of the centromeric region in a native state of the chromosome and a second side of the centromeric region when the chromosome has undergone a pericentric inversion, the step of determining the relative positioning including determining whether the telomeric region is on the second side of the centromeric region.

3. The method according to claim 1 wherein the telomeric and subcentromic regions occur on a same side of the centromeric region in a native state of the chromosome and opposite sides of the centromeric region when the chromosome has undergone a pericentric inversion, the step of determining the relative positioning including determining whether the telomeric and subcentromic regions are on opposite sides of the centromeric region.

4. The method according to claim 1 wherein the telomeric and subcentromic regions occur on opposite sides of the centromeric region in a native state of the chromosome and on a same side of the centromeric region of the chromosome has undergone a pericentric inversion, the step of determining the relative positioning including determining whether the telomeric and subcentromic regions are on the same side of the centromeric region.

5. The method according to claim 1 wherein determining the relative positioning of the first, second and third probes includes detecting a detectable marker on the first, second and third probes.

6. The method according to claim 5 wherein two of the first, second and third probes include the same detectable marker.

7. The method according to claim 5 wherein the telomeric and subcentromic regions occur on a same side of the centromeric region in a native state of the chromosome and opposite sides of the centromeric region when the chromosome has undergone a pericentric inversion, the step of determining the relative positioning including determining whether a third detectable marker appears between first and second detectable markers.

8. The method according to claim 5 wherein the telomeric and subcentromic regions occur on opposite sides of the centromeric region in a native state of the chromosome and on a same side of the centromeric region when the chromosome has undergone a pericentric inversion, the step of determining the relative positioning including determining whether a second detectable marker appears between first and third detectable markers.

9. The method according to claim 5 wherein at least one of the detectable markers is a fluorescent dye.

10. The method according to claim 1 wherein the step of contacting the first, second and third probes is done in the presence of blocking DNA.

11. A kit for detecting pericentric inversions in a chromosome comprising:
   a first probe having a sequence capable of selectively hybridizing to a telomeric region on either a first or second side of the chromosome relative to a centromeric region;
   a second probe having a sequence capable of selectively hybridizing to a subcentromeric region on either a first or second side of the chromosome relative to a centromeric region; and
   a third probe capable of selectively hybridizing to the centromeric region.

12. The kit according to claim 11 wherein the first and second probes are capable of selectively hybridizing on a same side of the chromosome relative to the centromeric region.

13. The kit according to claim 11 wherein the first and second probes are capable of selectively hybridizing on opposite sides of the chromosome relative to the centromeric region.

14. The kit according to claim 11 wherein the kit further includes blocking DNA.

15. The kit according to claim 11 wherein the first, second and third probes each independently include a detectable marker.

16. The kit according to claim 15 wherein two of the first, second and third probes include the same detestable marker.

17. The kit according to claim 16 wherein at least one of the detectable markers is a fluorescent dye.

* * * * *